United States Patent
Rada et al.

(10) Patent No.: US 11,207,451 B2
(45) Date of Patent: *Dec. 28, 2021

(54) MEDICAL APPARATUS FOR EXTRACORPOREAL TREATMENT OF FLUID AND A PROCESS OF CALCULATING SET FLOW RATES IN A MEDICAL APPARATUS FOR DELIVERY OR COLLECTION OF FLUIDS

(71) Applicant: GAMBRO LUNDIA AB, Lund (SE)

(72) Inventors: Hiram Rada, Lyons (FR); Dominique Pouchoulin, Tramoyes (FR); Georges Vantard, Villefontaine (FR); Alain Frugier, Chazay d'Azergues (FR)

(73) Assignee: Gambro Lundia AB, Lund (SE)

( * ) Notice: Subject to any disclaimer, the term of this patent is extended or adjusted under 35 U.S.C. 154(b) by 0 days.

This patent is subject to a terminal disclaimer.

(21) Appl. No.: 16/852,877

(22) Filed: Apr. 20, 2020

(65) Prior Publication Data
US 2020/0246529 A1   Aug. 6, 2020

Related U.S. Application Data

(60) Continuation of application No. 15/857,946, filed on Dec. 29, 2017, now Pat. No. 10,668,199, which is a
(Continued)

(30) Foreign Application Priority Data

Aug. 30, 2011 (EP) ..................................... 11007037

(51) Int. Cl.
*A61M 1/16* (2006.01)
*A61M 1/34* (2006.01)
(Continued)

(52) U.S. Cl.
CPC ............ *A61M 1/1613* (2014.02); *A61M 1/16* (2013.01); *A61M 1/1601* (2014.02);
(Continued)

(58) Field of Classification Search
CPC .............. A61M 1/1613; A61M 1/3609; A61M 1/3451; A61M 1/1605; A61M 1/1611;
(Continued)

(56) References Cited

U.S. PATENT DOCUMENTS 6,780,322 B1   8/2004  Bissler
8,668,825 B2   3/2014  Pouchoulin
(Continued)

FOREIGN PATENT DOCUMENTS

EP         2324871       5/2011
WO    WO 97/16220       5/1997
WO    WO 2007/073739    7/2007

*Primary Examiner* — Joseph W Drodge
(74) *Attorney, Agent, or Firm* — Mueting Raasch Group

(57) ABSTRACT

An apparatus for extracorporeal treatment of fluid and a process of setting up a medical apparatus for the delivery or collection of fluids are disclosed. According to the apparatus and the process, a control unit (10) is configured calculate set values of two or more of the fluid flow rates by imposing that an emptying time of containers of fresh fluid (16, 20, 21, 26) and/or a filling time of a waste container is substantially same as, or multiple of, the emptying time of one or more of the other containers of fresh fluid.

28 Claims, 11 Drawing Sheets

Related U.S. Application Data division of application No. 14/342,028, filed as application No. PCT/IB2012/001621 on Aug. 22, 2012, now abandoned.

(51) Int. Cl.
| | | |
|---|---|---|
| *B01D 61/30* | (2006.01) | |
| *B01D 61/32* | (2006.01) | |
| *A61M 1/36* | (2006.01) | |
| *G01F 1/00* | (2006.01) | |

(52) U.S. Cl.
CPC ........ *A61M 1/1605* (2014.02); *A61M 1/1611* (2014.02); *A61M 1/342* (2013.01); *A61M 1/3434* (2014.02); *A61M 1/3437* (2014.02); *A61M 1/3451* (2014.02); *A61M 1/3609* (2014.02); *B01D 61/30* (2013.01); *B01D 61/32* (2013.01); *G01F 1/00* (2013.01); *A61M 1/3441* (2013.01); *A61M 2202/0413* (2013.01); *A61M 2205/3331* (2013.01); *A61M 2205/3334* (2013.01); *A61M 2205/502* (2013.01); *A61M 2205/52* (2013.01); *A61M 2205/75* (2013.01)

(58) Field of Classification Search
CPC .............. A61M 1/1601; A61M 1/3434; A61M 1/3437; A61M 1/16; A61M 1/342; A61M 2205/502; A61M 2205/3331; A61M 2205/52; A61M 2202/0413; A61M 2205/75; A61M 1/3441; A61M 2205/3334; A61M 1/1603; A61M 1/3334; A61M 1/3403; A61M 1/3406; A61M 1/341; A61M 1/3424; A61M 1/3427; A61M 1/3607; A61M 2205/0431; A61M 2205/3341; B01D 61/30; B01D 61/32; B01D 61/24; B01D 61/243

USPC ................... 210/645, 646, 739, 741, 321.71; 604/4.01, 5.01, 6.01, 6.09, 6.11, 30, 31, 604/65, 67

See application file for complete search history.

(56) References Cited

U.S. PATENT DOCUMENTS

| | | | |
|---|---|---|---|
| 10,668,199 B2* | 6/2020 | Rada | .................... A61M 1/3437 |
| 2002/0088752 A1 | 7/2002 | Balschat | |
| 2004/0068219 A1 | 4/2004 | Summerton | |
| 2004/0182787 A1 | 9/2004 | Chevallet | |
| 2004/0267183 A1 | 12/2004 | Chevallet | |
| 2005/0095171 A1 | 5/2005 | Fressinet | |
| 2005/0131332 A1* | 6/2005 | Kelly | ...................... A61M 1/16 604/4.01 |
| 2006/0054215 A1 | 3/2006 | Remkes | |
| 2006/0124548 A1 | 6/2006 | Okazaki | |
| 2007/0062861 A1 | 3/2007 | Lannoy | |
| 2008/0149551 A1 | 6/2008 | Brugger | |
| 2008/0154170 A1 | 6/2008 | Lannoy | |
| 2009/0008306 A1* | 1/2009 | Cicchello | ............. A61M 1/1601 210/85 |
| 2009/0012453 A1* | 1/2009 | Childers | ................ A61M 1/288 604/29 |
| 2010/0280430 A1 | 11/2010 | Caleffi | |
| 2011/0017667 A1 | 1/2011 | Deimage | |
| 2011/0037968 A1 | 2/2011 | Li | |
| 2011/0112696 A1* | 5/2011 | Yodfat | ................... G16H 40/67 700/283 |
| 2011/0163034 A1 | 7/2011 | Castellamau | |
| 2012/0265117 A1* | 10/2012 | Fava | .................... A61M 1/3646 604/6.09 |
| 2015/0034557 A1 | 2/2015 | Pouchoulin | |

* cited by examiner

MEDICAL APPARATUS FOR EXTRACORPOREAL TREATMENT OF FLUID AND A PROCESS OF CALCULATING SET FLOW RATES IN A MEDICAL APPARATUS FOR DELIVERY OR COLLECTION OF FLUIDS

This application is a continuation of U.S. application Ser. No. 15/857,946, filed Dec. 29, 2017, which is a divisional of U.S. application Ser. No. 14/342,028, filed Jun. 3, 2014, which is a U.S. National Stage Application of International Application No. PCT/IB2012/001621, filed Aug. 22, 2012, which was published in English on Mar. 7, 2013 as International Patent Publication WO 2013/030643 A1. International Application No. PCT/IB2012/001621 also claims priority to European Application No. 11007037.2, filed Aug. 30, 2011. A certified copy of European Application No. 11007037.2 filed Aug. 30, 2011, was provided in, and is available in, U.S. patent application Ser. No. 14/342,028 for which certified copy is available in PAIR.

The present invention relates to a medical apparatus for extracorporeal processing of fluid, such as blood, a blood component or other biological or medical fluid. The present invention also relates to a process of calculating set flow rates in a medical apparatus for delivery, or collection, or for delivery and collection of fluids, such as for example in an apparatus for extracorporeal fluid processing.

In the field of biological fluid processing for medical use, several apparatuses are known which require manipulation of fluids of various nature. Known type of fluid processing system include extracorporeal blood treatment apparatus which are typically used to extract undesirable fluids and/or solutes from the patient's blood and/or add desirable fluids and/or substances to the blood. Extracorporeal blood treatment is used for treating patients unable to effectively remove excess water and undesirable substances from their blood, such as when a patient suffers temporary or permanent kidney failure. These patients may receive an extracorporeal blood treatment to add/or remove substances to their blood, to maintain an acid/base balance, and/or to remove excess body fluids, for example. Extracorporeal blood treatment is typically accomplished by removing the blood from the patient in e.g. a continuous flow, introducing the blood into a primary chamber, also referred to as blood chamber, of a filtration unit (such as a dialyzer or an hemofilter or an hemodiafilter) where the blood is allowed to flow along a semipermeable membrane. The semipermeable membrane selectively allows matter in the blood to cross the membrane from the primary chamber into a secondary chamber and also selectively allows matter in the secondary chamber to cross the membrane into the blood in the primary chamber, depending on the type of treatment. Cleared blood is then returned to the patient.

A number of different types of extracorporeal blood treatments may be performed. In an ultrafiltration (UF) treatment, undesirable fluids and substances is removed from the blood by convection across the membrane into the secondary chamber. In a hemofiltration (HF) treatment, the blood flows past the semipermeable membrane as in UF and desirable substances are added to the blood, typically by dispensing a fluid into the blood either via respective infusion lines before and/or after it passes through the filtration unit and before it is returned to the patient. In a hemodialysis (HD) treatment, a secondary fluid containing desirable substances is introduced into the secondary chamber of the filtration unit. Undesirable substances from the blood may cross the semipermeable membrane by diffusion into the secondary fluid and desirable substances from the secondary fluid may cross the membrane into the blood. In a hemodiafiltration (HDF) treatment, blood and secondary fluid exchange matter as in HD+UF, and, in addition, fluid is added to the blood, typically by dispensing it into the blood before its return to the patient as in HF.

To perform one or more of the above described treatments, extracorporeal blood treatment equipment may comprise a plurality of lines for delivering fluid directly to the patient or into the extracorporeal blood circuit.

When setting up the machine, an operator usually imposes the blood pump flow rate, the individual flow rates for each of the infusion lines, the flow rate for the dialysis line and for the effluent line (in reality this latter may alternatively be calculated based on the information of the set weight loss and treatment time or based on the set patient fluid removal rate). The set values for the flow rates on each line are used to control respective pumps: in other words, a plurality of pumps are used where each pump draws fluid from or supplies fluid to a respective fluid container according to the set flow rate value for the respective line.

As shown in FIG. 1A, representing a chart of the bag/container emptying times in an apparatus having three bags/containers and three respective fluid lines, each bag/container is emptied at a respective rate of fluid because consumption for each individual bag/container usually differs from that of the other bags. The consequence is that nurses or assisting operators are compelled to very frequently intervene to change a bag. The number of interventions for bag changes is directly proportional to the number of bags/containers used and leads to a very cumbersome management of the blood treatment equipment. In this respect it should also be noted that at each container change, the equipment, and thereby treatment delivery, must be stopped to give the operator time to substitute the container with a new one, thus leading to frequent interruptions with inefficient and discontinuous delivery of the treatment.

SUMMARY

In this situation, it is a general object of the present invention to offer a technical solution capable overcoming one or more of the above drawbacks.

In particular, it is an object of the present invention to render available a medical apparatus for the treatment of fluid and a process for calculating set flow rates in said apparatus capable of reducing as possible the frequency of container changes and consequent interruptions of treatment deliver.

It is an auxiliary object of the invention to offer a medical apparatus for the treatment of fluid and a process for calculating set flow rates in said apparatus which may facilitate flow rate setting before and during the treatment.

Another object of the invention is to offer a medical apparatus for the treatment of fluid and a process for calculating set flow rates in said apparatus capable of reducing treatment interruptions and bag or container changes without however compromising the prescribed treatment dose delivery.

Another object is an apparatus capable of controlling operating parameters in a safe manner.

At least one of the above objects is substantially reached by an apparatus according to one or more of the appended apparatus claims. One or more of the above objects is also substantially reached by a process according to any one of the appended process claims.

Apparatus and processes according to aspects of the invention are here below described.

A 1st aspect concerns an apparatus for extracorporeal treatment of blood comprising a filtration unit having a primary chamber and a secondary chamber separated by a semi-permeable membrane; a blood withdrawal line connected to an inlet of the primary chamber, and a blood return line connected to an outlet of the primary chamber said blood lines being configured for connection to a patient cardiovascular system; a blood pump configured to control the flow of blood through the blood lines; an effluent fluid line connected to an outlet of the secondary chamber; at least two further fluid lines selected in the group comprising:
- a pre-dilution infusion fluid line connected at one end thereof to the blood withdrawal line,
- a post-dilution infusion fluid line connected at one end thereof to the blood return line,
- a dialysis fluid line connected at one end thereof to the inlet of the secondary chamber,
- a pre-blood pump infusion fluid line connected at one end thereof to the blood withdrawal line in a region of this latter which is positioned in use upstream the blood pump, means, such as peristaltic pumps or flow regulating valves or centrifugal pumps, for regulating the flow of fluid through said fluid lines; and a control unit connected to the means for regulating, the control unit being configured to:
- allow entry by an operator of the set value for at least a first fluid flow rate selected in the group including:
  - a fluid flow rate $Q_{rep1}$ through the pre-dilution infusion fluid line,
  - a fluid flow rate $Q_{rep2}$ through the post-infusion fluid line,
  - a fluid flow rate $Q_{pbp}$ through the pre-blood pump infusion fluid line,
  - a fluid flow rate $Q_{dial}$ through the dialysis liquid fluid line, and
  - a fluid removal rate $Q_{pfr}$ from the patient,
- allow entry of a set value for a prescribed dose $D_{set}$ to be delivered,
- calculate set values of at least a second and a third of the fluid flow rates of said group of flow rates, based on the said first fluid flow rate set by the operator and on said prescribed dose value $D_{set}$.

In a 2nd aspect according to the 1st aspect the control unit is further configured to control said means for regulating the flow of fluid based on said set values of the fluid flow rates. In other words the control unit uses the calculated set values of the fluid flow rates for e.g. controlling the rotational pump of the pumps or the position of the regulating valves used on the fluid lines.

In a 3rd aspect according to any one of the preceding aspects a memory is provided storing a plurality of mathematical relations correlating fluid flow rates selected in said group, said control unit being connected to said memory.

In a 4th aspect according to the preceding aspect the control unit is further configured to calculate the set values at least of the second and third fluid flow rates by applying said prescribed dose value $D_{set}$ and the set value of the first fluid flow rate entered by the operator to said mathematical relations.

In a 5th aspect according to any one of the preceding two aspects, wherein said mathematical relations stored in said memory comprise one or more of the following:

- a convection-diffusion relation, relating the total fluid flow rate through said infusion fluid lines $Q_{rep1}+Q_{rep2}+Q_{pbp}$ with the fluid flow rate through said dialysis fluid line $Q_{dial}$,
- a blood pre-dilution relation, relating the flow rate of blood or of plasma $Q_{BLOOD}$, $Q_{PLASMA}$ and the fluid flow rate infused in the blood withdrawal line $Q_{rep1}+Q_{pbp}$ through said pre-dilution infusion fluid line and through said pre-blood pump infusion line,
- a pre post relation, relating the fluid flow rates $Q_{rep1}+Q_{pbp}$ through pre-dilution infusion fluid line and pre-blood pump infusion line with the fluid flow rate through the post-dilution infusion line $Q_{rep2}$.

In a 6th aspect according to the preceding aspects all said mathematical relations specified in the 5th aspect are stored in said memory.

In a 7th aspect according to any one of the preceding aspects from the 3rd to the 6th, the control unit is further configured to allow the user to select at least two of said relations and to calculate the set values of at least the second and third of said fluid flow rates by applying the set value of the prescribed dose and the set value of the first fluid flow rate entered by the operator to the mathematical relations selected by the user.

In a 8th aspect according to any one of the preceding aspects from the 5th to the 7th, the convection-diffusion relation defines a first ratio $R_1$ dividing the total fluid flow rate $Q_{rep1}+Q_{rep2}+Q_{pbp}$ through said infusion fluid lines by the fluid flow rate $Q_{dial}$ through said dialysis fluid line.

In a 9th aspect according to any one of the preceding aspects from the 5th to the 8th, the blood pre-dilution relation defines a second ratio $R_2$ dividing the flow rate of blood or of plasma $Q_{BLOOD}$, $Q_{PLASMA}$ by the sum of fluid flow rates $Q_{rep1}+Q_{pbp}$ infused in the blood withdrawal line through said pre-dilution infusion fluid line and through said pre-blood pump infusion line.

In a 10th aspect according to any one of the preceding aspects from the 5th to the 9th, the pre-post relation defines a third ratio $R_3$ dividing the sum of the fluid flow rates $Q_{rep1}+Q_{pbp}$ through said pre-blood pump infusion line and pre-dilution infusion line by the fluid flow rate $Q_{rep2}$ through said post-dilution infusion line.

In a 11th aspect according to any one of the preceding aspects from the 5th to the 10th, the control unit is further configured to: store a preset value or preset range for each one of said first, second and third ratios $R_1$, $R_2$, $R_3$.

In a 12th aspect according to any one of the preceding aspects from the 5th to the 11th, the control unit is further configured to allow entry by an operator of a set value or a set range for each one of said first, second and third ratios $R_1$, $R_2$, $R_3$.

In a 13th aspect according to any one of the preceding aspects the blood pump is active in correspondence of a segment of the blood withdrawal line and the apparatus comprises the following fluid lines:
- a pre-dilution infusion fluid line connected to the blood withdrawal line between the blood pump segment and the filtration unit,
- a post-dilution infusion fluid line connected to the blood return line,
- a dialysis fluid line connected to the inlet of the secondary chamber;

wherein the control unit is configured to calculate the set value for the fluid flow rate through each of the above-listed infusion lines which is not set by the operator based on said first fluid flow rate set by the operator and on said prescribed dose value $D_{set}$.

In a 14th aspect according to any one of the preceding aspects the blood pump is active in correspondence of a segment of the blood withdrawal line and the apparatus comprises the following fluid lines:
- a pre-dilution infusion fluid line connected to the blood withdrawal line between the blood pump segment and the filtration unit,
- a pre-blood pump infusion line connected to the blood withdrawal line in a region of this latter which is positioned in use upstream the blood pump segment,
- a post-dilution infusion fluid line connected to the blood return line,
- a dialysis fluid line connected to the inlet of the secondary chamber;

wherein the control unit is configured to calculate the set value for the fluid flow rate through each of the above-listed infusion lines which is not set by the operator based on said first fluid flow rate set by the operator and on said prescribed dose value $D_{set}$.

In a 15th aspect according to any one of the preceding aspects said prescribed dose value $D_{set}$ comprises a prescribed value for a flow rate or a combination of flow rates.

In a 16th aspect according to any one of the preceding aspects, said prescribed dose value $D_{set}$ comprises a prescribed value for one selected in the group including:
- an effluent dose flow rate $D_{eff\_set}$, which is the prescribed mean value of the flow rate through the effluent line,
- a convective dose flow rate $D_{conv\_set}$, which is the prescribed mean value of the sum of the flow rates through all infusion fluid lines $Q_{rep1}$, $Q_{rep2}$, $Q_{pbp}$ and the patient fluid removal rate $Q_{pfr}$, optionally wherein the prescribed convective dose flow rate value is corrected for predilution,
- a diffusive dose flow rate $D_{dial\_set}$: which is the prescribed mean value of the flow rate through the dialysis fluid line $Q_{dial}$,
- an urea dose $D_{urea\_set}$, which is a prescribed mean value for an estimated urea clearance,
- a clearance dose $K_{solute\_set}$, which is a prescribed mean value for an estimated clearance for a given solute.

In a 17th aspect according to the preceding aspect, the control unit is configured to correct the selected one of the above defined doses to take into account a predilution effect, when a fluid replacement or infusion line is present and delivers fluid upstream the treatment unit, by multiplying the dose value times a dilution factor $F_{dilution}$, which is < then 1, as per the following formula:

$$Dose_{corr\_xxx} = F_{dilution} \times Dose_{xxx} \text{ (with xxx=eff, conv, dial)}.$$

In a 18th aspect according to any one of the preceding aspects from the 3rd to the 17th, said first fluid flow rate is the fluid removal rate $Q_{pfr}$ from the patient and wherein the control unit is configured to receive the set value of the patient fluid removal rate $Q_{pfr}$ and to calculate the fluid flow rate $Q_{dial}$ through the dialysis liquid fluid line and the fluid flow rate $Q_{rep1}$, $Q_{pbp}$, $Q_{rep2}$ through the infusion fluid line or lines using at least two of said mathematical relations.

In a 19th aspect according to any one of the preceding aspects the control unit is further configured to allow entry by an operator of the set value for a blood flow $Q_{BLOOD}$ through the blood withdrawal or blood return line.

In a 20th aspect according to any one of the preceding aspects the control unit is configured to calculate the set value for the blood flow based on a sensed value of a patient parameter selected in the group comprising:
- blood pressure measured in a tract of the blood withdrawal line portion extending, in use, upstream the blood pump,
- a measured blood recirculation fraction re-circulating from the blood return line into the blood withdrawal line,
- a measured value of hemo-concentration measured in correspondence of one of the blood lines,
- a measured value of transmembrane pressure across the filter semipermeable membrane.

In a 21st aspect according to any one of the preceding two aspects the control unit is configured to control the blood pump using either the entered or the calculated set value for the blood flow $Q_{BLOOD}$.

In a 22nd aspect according to any one of the preceding aspects the control unit is further configured to calculate the set value for the fluid flow rate $Q_{pbp}$ through said pre-blood pump infusion line as a function of:
- the set or calculated value of flow rate of blood or of plasma $Q_{BLOOD}$, $Q_{PLASMA}$,
- a concentration $C_{citrate}$ of an anticoagulant, such as a citrate based solution, present in a container connected at an end of said pre-blood pump infusion line,
- a prescribed dose for said anticoagulant $D_{set-citrate}$, such as a citrate based solution, to be delivered through said pre-blood pump infusion line.

In a 23rd aspect according to any one of the preceding aspects from the 3rd to the 22nd, the apparatus further comprises a graphic user interface connected to said control unit, said control unit being configured to:
- display on the graphic user interface an indicium prompting a user to select the value for said first flow rate,
- display on the graphic user interface an indicium allowing selection of the mathematical relations the user intends to select,
- detecting selection of a mathematical relation and display an indicium allowing selection of a set value for one or more of said first, second and third ratios.

In a 24th aspect according to any one of the preceding aspects the means for regulating the flow of fluid through said fluid lines comprises a pre-dilution pump for regulating the flow through said pre-dilution fluid line and a post-dilution pump for regulating the flow through said post-dilution fluid line.

In a 25th aspect according to any one of the preceding aspects a dialysis fluid line is connected to the inlet of the secondary chamber, and the means for regulating the flow of fluid through said fluid lines comprises at least a dialysis fluid pump for regulating the flow through said dialysis fluid line.

In a 26th aspect according to any one of the preceding aspects said one or more infusion fluid lines comprise: a pre-blood pump infusion line connected to the blood withdrawal line in a region of this latter which is positioned in use upstream the blood pump, the means for regulating the flow of fluid through said fluid lines comprises at least a pre-blood infusion pump for regulating the flow through said pre-blood pump infusion line.

In a 27th aspect according to any one of the preceding aspects the apparatus further comprises a memory storing a one or a plurality of optimization criteria, said control unit being connected to said memory and being further configured to calculate the set values at least one of the second and third fluid flow rates by applying the optimization criteria.

In a 28th aspect according to any one of the preceding aspects, the apparatus includes a waste container connected to an end of the effluent fluid line.

In a 29th aspect according to any one of the preceding aspects, the apparatus includes a first container of fresh fluid connected to an end of the pre-dilution infusion fluid line.

In a 30th aspect according to any one of the preceding aspects, the apparatus includes a second container of fresh fluid connected to an end of the post-infusion fluid line.

In a 31st aspect according to any one of the preceding aspects, the apparatus includes a third container of fresh fluid connected to an end of the dialysis liquid fluid line.

In a 32nd aspect according to any one of the preceding aspects, the apparatus includes a fourth container of fresh fluid connected to an end of the pre-blood pump infusion fluid line.

In a 33rd aspect according to any one of the preceding aspects from the 27th to the 32nd, the optimization criteria comprises a first optimization criterion imposing that an emptying time of at least two among the containers of fresh fluid and, optionally, a filling time of the waste container are multiple of a same reference time.

In a 34th aspect according to any one of the preceding aspects from the 27th to the 32nd, the optimization criteria comprises a first optimization criterion imposing that an emptying time of at least one among the containers of fresh fluid and/or a filling time of the waste container is substantially same as or multiple of the emptying time of one or more of the other containers of fresh fluid.

In a 35th aspect according to any one of the preceding aspects from the 27th to the 34th the optimization criteria comprises a second optimization criterion imposing that fluid consumption through said fluid lines is minimized.

In a 36th aspect according to any one of the preceding aspects from the 27th to the 35th the optimization criteria comprises a third optimization criterion imposing that a life time of said filtration unit is maximized.

In a 37th aspect according to any one of the preceding aspects from the 27th to the 36th the optimization criteria comprises a fourth optimization criterion imposes that urea clearance or dialysance of a given solute is maximized.

In a 38th aspect according to any one of the preceding aspects from the 27th to the 37th the control unit is configured to allow the user selecting one or more of said criteria and calculate said at least second and third flow rate using said selected criteria.

In a 39th aspect according to any one of the preceding aspects from the 27th to the 37th allow the user selecting one or more of said criteria and one or more of said mathematical relations and to calculate said at least second and third flow rate using said selected criteria and said selected mathematical relations.

In a 40th aspect according to the preceding aspect the control unit is configured to determine if said selected criteria and said selected mathematical relations are compatible or conflicting and then:
in case the selected criteria and the selected mathematical relations are compatible, calculate the at least second and third flow rate based on the selected mathematical relations and optimization criteria,
in case one or more of the selected criteria is conflicting with one or more selected mathematical relations, execute one or more of the following sub-steps:
inform the user,
allow the user to assign a priority to each of the selected criteria or mathematical relations,
assign a priority ranking to the selected criteria and/or mathematical relations, said priority ranking being either predetermined or user adjustable, and then ignore criteria or mathematical relations as soon as flow rates have been calculated from the prioritized criteria/mathematical relations,
define a compromise between conflicting criteria and mathematical relations using preset rules.

In a variant of the invention it should be noted that the control unit may be configured combine the use of the flow rate set-up procedure with the use of one or more optimization criteria. For example the control unit may be configured to:
execute said flow-rate setup (see previous aspects) procedure to calculate set values for a plurality of flow rates of said group and, at least for a first time interval, control the means for regulating the flow of fluid (17, 18, 21, 24, 27) based on the set values calculated executing the flow-rate setup procedure; and then
allow selection of one optimization criteria, for instance the first optimization criterion, to calculate the set values for a plurality of flow rates using the selected optimization criterion, for then (at least for a second time interval subsequent to the first time interval) controlling said means for regulating the flow of fluid (17, 18, 21, 24, 27) based on the set values calculated based on the selected optimization criterion.

A 41st aspect relates to an apparatus for extracorporeal treatment of fluid comprising:
a filtration unit having a primary chamber and a secondary chamber separated by a semi-permeable membrane; a blood withdrawal line connected to an inlet of the primary chamber, and a blood return line connected to an outlet of the primary chamber said blood lines being configured for connection to a patient cardiovascular system;
a blood pump configured to control the flow of blood through the blood lines;
an effluent fluid line connected, at one end thereof, to an outlet of the secondary chamber and, at its other end, optionally connected to a waste container;
at least two further fluid lines selected in the group of fluid lines comprising:
a pre-dilution infusion fluid line connected at one end thereof to the blood withdrawal line and at its other end to a first container of fresh fluid,
a post-dilution infusion fluid line connected at one end thereof to the blood return line and at its other end to a second container of fresh fluid,
a dialysis fluid line connected at one end thereof to the inlet of the secondary chamber and at its other end to a third container of fresh fluid,
a pre-blood pump infusion fluid line connected at one end thereof to a fourth container of fresh fluid and at its other end to the blood withdrawal line in a region of this latter which is positioned in use upstream the blood pump,
one or more syringe lines (50) connected at one end thereof either to the blood withdrawal line (6) or to the blood return line (7) or directly to the patient, and at its other end to a syringe container (S),
means for regulating the flow of fluid (17, 18, 21, 22, 27, P) through one or more said fluid lines (13, 15, 21, 25, 19); and
a control unit (10) connected to the means for regulating, the control unit being configured to:
calculate set values ($Q_{iset}$) of two or more of the fluid flow rates selected in the group of fluid flow rates including:
a fluid flow rate ($Q_{rep1}$) through the pre-dilution infusion fluid line (15), a fluid flow rate ($Q_{rep2}$) through the post-infusion fluid line (25), a fluid flow rate ($Q_{pbp}$) through the pre-blood pump infusion fluid line (21), a fluid flow rate ($Q_{dial}$) through the dialysis liquid fluid line (27), a fluid flow rate ($Q_{syr}$) through the syringe fluid line (50), a fluid flow rate ($Q_{eff}$) through the effluent fluid line (13), by imposing that emptying times of at least two among the containers of fresh fluid (16, 20, 21, 26, S) and, optionally, the filling time of the waste container are multiple of a same reference time ($T_r$).

By defining the reference time $T_r$ and a multiplication factor, it is possible to define in relation to each fresh fluid line e.g. the following:

an emptying time of the respective container which is the same of the emptying time of a container relating to another line, an emptying time of the respective container which is the multiple of the emptying time of a container relating to another line, an emptying time of the respective container which is a fraction (A/B where both A and B are integers) of the emptying time of a container relating to another line.

Optionally the above relations may be applied, mutatis mutandis, to the filling time of the waste container.

In a 42$^{nd}$ aspect according to the 41$^{st}$ aspect the control unit is configured to:

calculate the set values of (N−1) of said fluid flow rates ($Q_{iset}$) by imposing that an emptying time of at least one among the containers of fresh fluid (16, 20, 21, 26) is substantially same as, or multiple of the emptying time of one or more of the other containers of fresh fluid; note that alternatively said empting time may be imposed to be substantially same as, or multiple of one selected among: the emptying time of one or more of the other containers of fresh fluid, and the filling time of the waste container; also note that the reference time ($T_r$) may be the shortest among said empting times; and calculate the remaining of said fluid flow rates ($Q_{iset}$) by applying a fluid balance equation imposing that the sum of the fluid flow rates through fluid lines coming from fresh fluid containers ($Q_{rep1}$, $Q_{rep2}$, $Q_{dial}$, $Q_{pbp}$) and of a patient fluid removal rate ($Q_{pfr}$) is equal to the effluent fluid line flow rate ($Q_{eff}$):

$$\Sigma(Q_{repi} + Q_{dial} + Q_{pbp} + Q_{pfr}) = Q_{eff}.$$

In a 43$^{rd}$ aspect according to the 41$^{st}$ aspect the control unit is configured to:

calculate the set values of (N−1) of said fluid flow rates ($Q_{iset}$) by imposing that an emptying time of at least one among the containers of fresh fluid (16, 20, 21, 26) is substantially same as, or multiple of the filling time of the waste container, and calculate the remaining of said fluid flow rates ($Q_{iset}$) by applying a fluid balance equation imposing that the sum of the fluid flow rates through fluid lines coming from fresh fluid containers ($Q_{rep1}$, $Q_{rep2}$, $Q_{dial}$, $Q_{pbp}$) and of a patient fluid removal rate ($Q_{pfr}$) is equal to the effluent fluid line flow rate ($Q_{eff}$):

$$\Sigma(Q_{repi} + Q_{dial} + Q_{pbp} + Q_{pfr}) = Q_{eff}.$$

In a 44$^{th}$ aspect, according to any one of the preceding three aspects, the control unit is configured to use at least two reference times $T_{r1}$ and $T_{r2}$. This solution may be adopted when the apparatus includes at least four of the fluid lines selected in said group of fluid lines specified in aspect 41. The control unit is configured to calculate set values ($Q_{iset}$) of two or more of:

a fluid flow rate ($Q_{rep1}$) through the pre-dilution infusion fluid line (15), a fluid flow rate ($Q_{rep2}$) through the post-infusion fluid line (25), a fluid flow rate ($Q_{pbp}$) through the pre-blood pump infusion fluid line (21), a fluid flow rate ($Q_{dial}$) through the dialysis liquid fluid line (27), a fluid flow rate ($Q_{syr}$) through the syringe fluid line (50), a fluid flow rate ($Q_{eff}$) through the effluent fluid line (13), by imposing that the emptying times of at least two among the containers of fresh fluid (16, 20, 21, 26, S) and, optionally, the filling time of the waste container are multiple of a first reference time ($T_{r1}$) and also imposing that that emptying times of at least two other among the containers of fresh fluid (16, 20, 21, 26, S) and, optionally, the filling time of the waste container are multiple of a second reference time ($T_{r2}$).

In other words, in accordance with this aspect it is possible to synchronize the emptying of two or more containers (e.g. container 16 and 20) of fresh fluid with reference to a first reference time such that for instance the emptying time of said two containers is multiple of the first reference time, while the emptying two or more other containers (e.g. containers 21 and 26, or 21, 26 and S) may be synchronized with reference to a second reference time such that for instance the emptying time of said two other containers is multiple of the second reference time. This may still allow a good degree of overall synchronization and time saving. Of course it is also possible to synchronize the filling of the waste container with reference to either one of the two reference times.

In principle, if the apparatus would include a relevant number of lines bringing and or withdrawing fluid from the blood circuit and leading to respective fresh fluid containers or waste containers, it may be possible to synchronize the emptying/filling of the containers in 3 or more groups where each group of containers is synchronized relative to a respective reference time.

In a 45$^{th}$ aspect according to any one of the aspects from the 41$^{st}$ to the 44$^{th}$, the control unit is further configured to control said means for regulating based on said calculated set values, either automatically or after receipt of a confirmation signal.

In a 46$^{th}$ aspect according to any one of the aspects from the 41$^{st}$ to the 45$^{th}$ the apparatus comprises at least the following fluid lines:

a pre-dilution infusion fluid line connected to the blood withdrawal line, a post-dilution infusion fluid line connected to the blood return line, a dialysis fluid line connected to the inlet of the secondary chamber.

In a 47$^{th}$ aspect according to any one of the aspects from the 41$^{st}$ to the 46$^{th}$ the control unit is configured to calculate the set value for the fluid flow rate through each of the infusion fluid lines and dialysis fluid line by imposing that the emptying time of each given of said first, second and third containers is multiple of the same reference time $T_r$.

In a 48$^{th}$ aspect according to any one of the aspects from the 41$^{st}$ to the 46$^{th}$ the control unit is configured to calculate the set value for the fluid flow rate through each of the infusion fluid lines and dialysis fluid line by imposing that the emptying time of each given of said first, second and third containers is same as or multiple of the emptying time of one or more other of said first, second and third containers.

In a 49th aspect according to any one of the preceding aspects the blood pump is active in correspondence of a segment of the blood withdrawal line, the pre-dilution infusion fluid line is connected to the blood withdrawal line between the blood pump segment and the filtration unit, and a pre-blood pump infusion fluid line is connected to the blood withdrawal line in a region of this latter which is positioned between the blood pump segment and an end of the blood withdrawal line opposite the end connected to the filtration unit.

In a 50th aspect according to any one of the preceding aspects the control unit is configured to calculate the set value for the fluid flow rate through each of the infusion fluid lines and dialysis fluid line by imposing that the emptying time of each given of said first, second, third, and fourth containers is multiple of the same reference time $T_r$.

In a 51st aspect according to the preceding aspect the control unit is configured to calculate the set value for the fluid flow rate through each of the infusion fluid lines and dialysis fluid line by imposing that the emptying time of each given of said first, second, third, and fourth containers is same as or multiple of the emptying time of one or more other of said first, second, third, and fourth containers.

In a 52nd aspect according to the preceding aspect the waste line is connected to the waste container and the control unit is configured to calculate the set value for the fluid flow rate through each of the fluid lines by imposing that the emptying time of each given of said containers of fresh fluid and the filling time of the waste container are multiple of the same reference time $T_r$ and are optionally same as or multiple of the emptying time of one or more other containers of fresh fluid or filling time of the waste container.

In a 53rd aspect according to any one of the preceding aspects the control unit is configured to store in a memory connected to the control unit the volume or weight of fluid which may be contained in each container of fresh fluid and optionally in said waste container.

In a 54th aspect according to the preceding aspect, said volume or weight of fluid is detected by a sensor associated to each respective container and connected to the control unit, or said volume or weight of fluid is entered by an operator for each respective container through a user interface connected to the control unit.

In a 55th aspect according to the 53rd aspect, said volume or weight of fluid is determined by the control unit associating an identification code on each respective container to a respective volume.

In a 56th aspect according to the 53rd aspect, said volume or weight of fluid is pre-stored in said memory.

In a 57th aspect according to any one of the preceding aspects the control unit is further configured to receive, for instance by allowing a corresponding selection by an operator, at least one set value for a treatment time T.

In a 58th aspect according to any one of the preceding aspects the control unit is further configured to receive, for instance by allowing a corresponding selection by an operator, at least one set value for a treatment dose $D_{set}$ to be delivered to the patient during the treatment.

In a 59th aspect according to the preceding aspect the set value for the treatment dose comprises a prescribed value for one selected in the group including:
an effluent dose flow rate $D_{eff\_set}$, which is the prescribed mean value of the flow rate through the effluent line,
a convective dose flow rate $D_{conv\_set}$, which is the prescribed mean value of the sum of the flow rates through any infusion fluid line $Q_{rep}$, $Q_{pbp}$ and the patient fluid removal rate $Q_{pfr}$,
a diffusive dose flow rate $D_{dial\_set}$, which is the prescribed mean value of the flow rate through the dialysis fluid line $Q_{dial}$,
an urea dose $D_{urea\_set}$, which is a prescribed mean value for an estimated urea clearance,
a clearance dose $K_{solute\_set}$, which is a prescribed mean value for an estimated clearance for a given solute.

In a 60th aspect according to any one of the preceding aspects the control unit is further configured to receive, for instance by allowing a corresponding selection by an operator, at least one set value for one or more of:
a fluid flow rate $Q_{rep1}$ through the pre-dilution infusion fluid line;
a fluid flow rate $Q_{rep2}$ through the post-infusion fluid line;
a fluid flow rate $Q_{pbp}$ through the pre-blood pump infusion fluid line;
a fluid flow rate $Q_{dial}$ through the dialysis liquid fluid line;
a fluid flow rate $Q_{eff}$ through the effluent fluid line.

In a 61st aspect according to any one of the preceding aspects the apparatus comprises one or more scales weighing one or more of said containers.

In a 62nd aspect according to any one of the preceding aspects the apparatus comprises a corresponding scale for each respective of said containers, said one or more scales being connected to the control unit and sending to the control unit corresponding weight signals.

In a 63rd aspect according to any one of the preceding aspects the control unit is configured to:
receive an initial weight or volume $W_i$, $V_i$ of one or more of said containers,
calculate the set value of the fluid flow rate $Q_{iset}$ in one or more of said fluid lines dividing a weight or volume $W_i$, $V_i$ of the respective container by the value of the reference time $T_r$ using formula: $Q_{iset}=W_i/T_r$ or $Q_{iset}=V_i/T_r$.

In a 64th aspect according to any one of the preceding aspects the control unit is configured to:
receive an initial weight or volume $W_i$, $V_i$ of one or more of said containers,
calculate the set value of the fluid flow rate $Q_{iset}$ in one or more of said fluid lines
or dividing a weight or volume $W_i$, $V_i$ of the respective container by the value of a reference time $T_r$ multiplied by a respective weighing coefficient $c_i$ for each respective container using formula:

$$Q_{iset}=W_i/(T_r \cdot C_i)$$

or $$Q_{iset}=W_i/(T_r \cdot c_i)$$

In a 65th aspect according to any one of the preceding aspects the control unit is configured to:
receive an initial weight or volume $W_i$, $V_i$ of one or more of said containers,
receive proposed values $Q_i$ of the flow rates for said fluid lines;
calculate the set value of the fluid flow rate $Q_{iset}$ in one or more of said fluid lines dividing a weight or volume $W_i$, $V_i$ of the respective container by the value of the reference time $T_r$ multiplied by a respective weighing coefficient $c_i$ for each respective container using formula:

$$Q_{iset}=W_i/(T_r \cdot c_i),$$

or $$Q_{iset}=V_i/(T_r \cdot c_i),$$

where the weighing coefficient $c_i$ for each respective container is calculated as a function of an intermediary factor $b_i$ obtained by dividing either the dose or the sum of said proposed values $Q_i$ of the flow rates by the respective proposed value $Q_i$, optionally wherein the weighing coefficient $c_i$ for each respective container is calculated using formula:

$$C_i=\text{Round}[b_i/\min(b_1 \ldots b_n)],$$

where:
"$\min(b_1 \ldots b_n)$" is a function selecting the minimum among the $b_i$ factors, and
"Round" calculates the natural number nearest to the result of quotient $b_i/\min(b_1 \ldots b_5)$.

In a 66$^{th}$ aspect according to any one of the preceding aspects the control unit is configured to:
receive an initial weight or volume $W_i$, $V_i$ of one or more of said containers,
receive proposed values $Q_i$ of the flow rates for said fluid lines;
receive the value of an adjustment parameter A defined as maximum relative change allowed on container change periods;
calculate the set values of said fluid flow rates $Q_{iset}$ based on the proposed values $Q_i$, the initial weight or volume $W_i$, $V_i$ of each container and the value of the adjustment parameter A.

A 67$^{th}$ aspect relates to an apparatus for extracorporeal treatment of fluid comprising:
a filtration unit having a primary chamber and a secondary chamber separated by a semi-permeable membrane;
a blood withdrawal line connected to an inlet of the primary chamber, and a blood return line connected to an outlet of the primary chamber said blood lines being configured for connection to a patient cardiovascular system;
a blood pump configured to control the flow of blood through the blood lines;
an effluent fluid line connected, at one end thereof, to an outlet of the secondary chamber and, at its other end, optionally connected to a waste container;
at least two further fluid lines selected in the group comprising:
 a pre-dilution infusion fluid line connected at one end thereof to the blood withdrawal line and at its other end to a first container of fresh fluid,
 a post-dilution infusion fluid line connected at one end thereof to the blood return line and at its other end to a second container of fresh fluid,
 a dialysis fluid line connected at one end thereof to the inlet of the secondary chamber and at its other, end to a third container of fresh fluid,
 a pre-blood pump infusion fluid line connected at one end thereof to a fourth container of fresh fluid and at its other end to the blood withdrawal line in a region of this latter which is positioned in use upstream the blood pump,
 one or more syringe lines (50) connected at one end thereof either to the blood withdrawal line (6) or to the blood return line (7) or directly to the patient, and at its other end to a syringe container (S),
means for regulating the flow of fluid through one or more said fluid lines; and
a control unit connected to the means for regulating, the control unit being configured to calculate set values $Q_{iset}$ of two or more of the fluid flow rates selected in the group including:
 a fluid flow rate $Q_{rep1}$ through the pre-dilution infusion fluid line,
 a fluid flow rate $Q_{rep2}$ through the post-infusion fluid line,
 a fluid flow rate $Q_{pbp}$ through the pre-blood pump infusion fluid line,
 a fluid flow rate $Q_{dial}$ through the dialysis liquid fluid line,
 a fluid flow rate ($Q_{syr}$) through the syringe fluid line,
 a fluid flow rate $Q_{eff}$ through the effluent fluid line,
by executing the following steps:
 receiving an initial weight or volume $W_i$, $V_i$ of one or more of said containers,
 receiving proposed values $Q_i$ of the flow rates for said fluid lines;
 receiving the value of an adjustment parameter A defined as maximum relative change allowed on container change periods;
 calculating the set values of said fluid flow rates $Q_{iset}$ based on the proposed values $Q_i$, the initial weight or volume $W_i$, $V_i$ of each container and the value of the adjustment parameter A.

In a 68$^{th}$ aspect according to any one of the preceding aspects the control unit is configured to
receive an initial weight or volume $W_i$, $V_i$ of one or more of said containers,
receive proposed values $Q_i$ of the flow rates for said fluid lines, which may be either entered by the user or come from a previous calculation step, e.g. using the mathematical relations mentioned in some of the above aspects,
for each pair of lines and respective containers, generate ratios of interest $R0_k$, which are reference ratios between change periods of pairs of containers and are defined for each pair of lines and respective containers, K being an integer from 1 to M, with the value of M pre-stored in the control unit memory or receivable from a user input;
calculate the containers change periods $T_i=V_i/Q_i$ or $T_i=W_i/Q_i$ and rank each circuit according to the calculated container change period, where i=1 to N with $T_i$ increasing with i and N is the number of lines to which the calculation (that is the synchronization sequence) applies;
compute all period ratios $R_{ij}=T_i/T_j$, with i>j;
compare each period ratio $R_{ij}$ to the ratios of interest $R0_k$;
verify if there is a k value verifying that $R_{ij}/R0_k$ stays within a tolerance limit (selectable by the user or preset in a memory of the computer unit),
compute the number of daily saved container changes and selecting the ratios $R_{ij}$ providing the largest number of saved container changes and respecting the above tolerance limit;
apply the ratios of interest corresponding to the selected ratios $R_{ij}$ to compute the optimized flow rates $Q_{iset}$.

In a 69$^{th}$ aspect according to any one of the preceding aspects the control unit is configured to:
receive an initial weight or volume $W_i$, $V_i$ of one or more of said containers,
receive proposed values $Q_i$ of the flow rates for said fluid lines, which may be either entered by the user or come from a previous calculation step, e.g. using the mathematical relations mentioned in some of the above aspects, for each pair of lines and respective containers, generate ratios of interest $R0_k$, which are reference ratios between change periods of pairs of containers and are defined for each pair of lines and respective containers, K being an integer from 1 to M, with the value of M pre-stored in the control unit memory or receivable from a user input;

calculate the containers change periods $T_i=V_i/Q_i$ or $T_i=W_i/Q_i$ and rank each circuit according to the calculated container change period, where i=1 to N with $T_i$ increasing with i and N is the number of lines to which the calculation (that is the synchronization sequence) applies;

compute all period ratios $R_{ij}=T_i/T_j$, with i>j;

compare each period ratio $R_{ij}$ to the ratios of interest $R0_k$;

for each ratio $R_{ij}$ where a k value exists verifying the tolerance relation: $(1-A) \cdot R0_k < R_{ij} < (1+A) \cdot R0_k$, compute the number of daily saved container changes;

select the ratios $R_{ij}$ providing the largest number of saved container changes;

apply the ratios of interest corresponding to the selected ratios to compute the optimized flow rates $Q_{iset}$.

In a 70$^{th}$ aspect according to any one of the preceding aspects from the 41$^{st}$ to the 69$^{th}$ said control unit is configured to:

allow entry of the treatment time T, calculate the reference time $T_r$ either as the treatment time T or as a sub-multiple of the treatment time T.

In a 71$^{st}$ aspect according to any one of the preceding aspects from the 41$^{st}$ to the 70$^{th}$ the control unit is configured to receive one set value set by an operator for one fluid flow rate selected in the group comprising:

a fluid flow rate $Q_{rep1}$ through the pre-dilution infusion fluid line, a fluid flow rate $Q_{rep2}$ through the post-infusion fluid line, a fluid flow rate $Q_{pbp}$ through the pre-blood pump infusion fluid line, a fluid flow rate $Q_{dial}$ through the dialysis liquid fluid line;

identifying the container associated to the fluid line for which the fluid flow rate has been set by the operator; and calculating the reference time $T_r$ dividing the initial weight or volume $W_i$, $V_i$ of the identified container by the set value of the fluid flow rate set by the operator.

In a 72$^{nd}$ aspect according to any one of the preceding aspects from the 41$^{st}$ to the 71$^{st}$ the control unit is configured to compute the reference time $T_r$ by:

dividing the sum of the initial weights or volumes $W_i$, $V_i$ of a plurality of said containers by the prescribed dose flow rate value which is set to be delivered in total through the lines $D_{conv\_set}$ leading to the same plurality of containers, or dividing the sum of the initial weights or volumes $W_i$, $V_i$, of all said containers by the total prescribed dose flow rate $D_{eff\_set}$, or dividing the weighed sum of the initial weights or volumes $W_i$ of a plurality of said containers by the prescribed dose flow rate value which is set to be delivered in total through the lines $D_{conv\_set}$ leading to the same plurality of containers, using formula:

$T_r = \Sigma W_i \cdot c_i / \text{Dose}$ where $c_i$ is an weighing coefficient to be multiplied by the initial weight or volume of each container; or dividing the weighed sum of the initial weights or volumes $W_i$, $V_i$ of all said containers by the total prescribed dose flow rate $D_{eff\_set}$, using formula:

$T_r = \Sigma W_i \cdot c_i / \text{Dose}$ where $c_i$ is the weighing coefficient to be multiplied by the initial weight or volume of each container.

In a 73$^{rd}$ aspect according to any one of the preceding aspects from the 41$^{st}$ to the 72$^{nd}$ wherein the apparatus comprises a separate scale detecting the weight of each respective container.

In a 74$^{th}$ aspect according to the preceding aspect, the control unit is configured to receive a weight $W_i$ of one or more of said containers as measured by a corresponding scale associated to each container, wherein the weight of each respective container $W_i$ used for the calculation of the set values of the fluid flow rates is determined either at the beginning of the treatment or at a prefixed checkpoint during treatment or responsive to a user input.

In a 75$^{th}$ aspect according to one of the preceding two aspects the control unit is configured to compare the detected weight of each container of fresh fluid to a respective threshold and to determine that a fresh fluid container is empty if the detected weight is below the respective threshold.

In a 76$^{th}$ aspect according to one of the preceding three aspects the control unit is configured to compare the detected weight of the waste fluid container a respective threshold and to determine that the waste container is full if the detected weight is above the threshold. The threshold may be fixed or the control unit may be configured to calculate as threshold a set value ($N_{eff\-change}$) of the waste container reference volume or weight, at which the control unit considers that the waste container is full, by imposing that the filling time of the waste container is substantially same as, proportional to, or multiple of the emptying time of one or more of the other containers of fresh fluid.

In a 77$^{th}$ aspect according to one of the preceding two aspects the control unit is configured to generate an empty container signal when the weight of one or more containers of fresh fluid is below the respective threshold and to generate a full container signal when the weight of said waste container is above the respective threshold.

In a 78$^{th}$ aspect according to any one of the preceding aspects the means for regulating the flow of fluid through said fluid lines comprises a pre-dilution pump for regulating the flow through said pre-dilution fluid line and a post-dilution pump for regulating the flow through said post-dilution fluid line, a dialysis fluid line is connected to the inlet of the secondary chamber, and the means for regulating the flow of fluid through said fluid lines comprises at least a dialysis fluid pump for regulating the flow through said dialysis fluid line, said one or more infusion fluid lines comprise a pre-blood pump infusion line connected to the blood withdrawal line in a region of this latter which is positioned in use upstream the blood pump, and the means for regulating the flow of fluid through said fluid lines comprises at least a pre-blood infusion pump for regulating the flow through said pre-blood pump infusion line.

In a 79$^{th}$ aspect according to any one of the preceding aspects the control unit is further configured to:

allow entry by an operator of the set value for a blood flow $Q_{BLOOD}$ through the blood withdrawal or blood return line, or calculate the set value for the blood flow based on a sensed value of a patient parameter selected in the group comprising:
- blood pressure measured in a tract of the blood withdrawal line portion extending, in use, upstream the blood pump,
- a measured blood recirculation fraction re-circulating from the blood return line into the blood withdrawal line,
- a measured value of hemo-concentration measured in correspondence of one of the blood lines,
- a measured value of transmembrane pressure across the filter semipermeable membrane, control the blood pump using either the entered or the calculated set value for the blood flow $Q_{BLOOD}$.

In a 80$^{th}$ aspect according to any one of the preceding aspects said control unit is configured to allow entry of:
a) the fluid removal rate $Q_{pfr}$ from the patient, or of
b) the treatment time T and of the weight loss WL to be imposed over said treatment time T. In this second case the fluid removal rate may be calculated as ratio between WL and T.

In a 81$^{st}$ aspect according to any one of the preceding aspects
the control unit is further configured to calculate the set values ($Q_{iset}$) of the fluid flow rates through said fluid lines by imposing that:
- the emptying times of the containers of fresh fluid (16, 20, 21, 26) are multiple of a same reference time ($T_r$), and
- the sum of the fluid flow rates ($Q_{rep1}$, $Q_{rep2}$, $Q_{pbp}$) through the infusion fluid lines present in the apparatus $Q_{rep2}$, (15, 25, 21) plus the fluid flow rate 10 through the dialysis line (19), if present, plus the fluid removal rate ($Q_{pfr}$) from the patient equals ($Q_{eff}$) the fluid flow rate through the effluent fluid line (13).

In a 82$^{nd}$ aspect according to any one of the preceding aspects all containers of fresh fluid comprise a fluid having a same composition.

Alternatively, the fourth container of fresh fluid comprises a fluid having a composition different from that of the other containers of fresh fluid, for example said fourth container contains an anticoagulant (heparin or a regional anticoagulant such as a citrate solution): in this case the control unit is configured to calculate the set value of fluid flow rate through the pre-blood pump infusion line based on a pre-defined algorithm: e.g. the flow rate through the pre-blood pump infusion line may be set to be proportional to the set or calculated value of the blood pump flow rate. In a further alternative if the apparatus comprises the fourth container which includes a regional anticoagulant, for example a citrate based solution, then the second container leading to said post-dilution infusion fluid line includes an ionic balance solution, for example calcium ion based solution: in this case the control unit is configured to calculate the fluid flow rate through said pre-blood pump infusion fluid line and through said post-dilution infusion fluid line based on pre-defined algorithm(s).

In a 83$^{rd}$ aspect according to any one of the preceding aspects the apparatus comprises one or two syringe lines leading to respective syringe containers (S) including an anticoagulant solution or a ionic balance solution, the control unit being configured to calculate the fluid flow rate through said syringe line or lines based on pre-defined algorithm(s).

In a 84$^{th}$ aspect according to any one of the preceding aspects the control unit is configured to check if the calculated set value for the fluid flow rate through the post-dilution infusion line is higher than a prefixed fraction of the blood flow rate.

In a 85$^{th}$ aspect according to the preceding aspect wherein if the calculated set value for the fluid flow rate through the post-dilution infusion line is higher than a prefixed fraction of the blood flow rate, the control unit is configured to activate a correction procedure comprising:
- correcting the delivery of fluid through one or more of the other lines, or
- temporary connecting the post-dilution fluid line to the blood withdrawal line.

In a 86$^{th}$ aspect according to any one of the preceding aspects the control unit is configured to:
- associate to each container a reference volume or a reference weight which, when reached by the respective container, triggers a container change signal, and
- compare a measured volume or weight of each container to the respective reference volume or reference weight to trigger a container change signal container when the container reaches the respective reference volume or a reference weight;
- further wherein the control unit is configured to impose on one or more containers of fresh fluid a reference volume or reference weight which is different from zero and/or on the waste container a reference volume or weight which is less than the maximum volume ore weight of the waste container. For instance the control unit is configured to calculate a set value ($N_{eff-change}$) of the waste container reference volume or weight, at which the control unit considers that the waste container is full, by imposing that the filling time of the waste container is substantially same as, proportional to, or multiple of the emptying time of one or more of the other containers of fresh fluid.

A 87$^{th}$ aspect concerns a process of setting up a medical apparatus for the delivery and/or collection of fluids, the apparatus comprising:
- a plurality of fluid lines connected at one end thereof a respective container,
- a pump or a valve regulator configured to regulate the flow of fluid through said fluid lines; the process comprising the following steps:
  - calculating set values of two or more of the fluid flow rates through said lines by imposing that an emptying time and/or a filling time of at least one among the containers is substantially same as, proportional to or multiple of, the emptying time of one or more of the other containers,
  - storing said calculated set values in identified retrievable memory locations of said apparatus for subsequent use to control said pump or valve regulator.

In a 88$^{th}$ aspect according to the preceding aspect, the apparatus comprises:
- a filtration unit having a primary chamber and a secondary chamber separated by a semi-permeable membrane;
- a blood withdrawal line connected to an inlet of the primary chamber, and a blood return line connected to an outlet of the primary chamber said blood lines being designed to be connected to a patient cardiovascular system;
- a blood pump configured to control the flow of blood through the blood lines;

an effluent fluid line connected, at one end thereof, to an outlet of the secondary chamber and, at its other end, optionally connected to a waste container;

at least two fluid lines selected in the group comprising:
- a pre-dilution infusion fluid line connected at one end thereof to the blood withdrawal line and at its other end to a first container,
- a post-dilution infusion fluid line connected at one end thereof to the blood return line and at its other end to a second container,
- a dialysis fluid line connected at one end thereof to the inlet of the secondary chamber and at its other end to a third fluid container,
- a pre-blood pump infusion line connected at one end thereof to a fourth container and at its other end to the blood withdrawal line in a region of this latter which is positioned in use upstream the blood pump,
- one or more syringe lines (50) connected at one end thereof either to the blood withdrawal line (6) or to the blood return line (7) or directly to the patient, and at its other end to a syringe container (S);

the pump or a valve regulator being configured to regulate the flow of fluid through said fluid lines and a control unit being connected to the pump or valve regulator, wherein the process is executed by the control unit and comprises the following steps:
calculating set values of two or more of the fluid flow rates selected in the group including:
- a fluid flow rate $Q_{rep1}$ through the pre-dilution infusion fluid line,
- a fluid flow rate $Q_{rep2}$ through the post-infusion fluid line,
- a fluid flow rate $Q_{pbp}$ through the pre-blood pump infusion fluid line,
- a fluid flow rate $Q_{dial}$ through the dialysis liquid fluid line,
- a fluid flow rate $Q_{syr}$ through the syringe fluid line(s) (50),
- a fluid flow rate $Q_{eff}$ through the effluent fluid line, by imposing that an emptying time of at least one among the containers of fresh fluid and/or a filling time of the waste container is substantially same as, or multiple of, the emptying time of one or more of the other containers of fresh fluid, storing said calculated set values in identified retrievable memory locations for subsequent use to control said means for regulating the flow of fluid.

In a 89$^{th}$ aspect according to the preceding aspect, the apparatus comprises:

a filtration unit having a primary chamber and a secondary chamber separated by a semi-permeable membrane;

a blood withdrawal line connected to an inlet of the primary chamber, and a blood return line connected to an outlet of the primary chamber said blood lines being designed to be connected to a patient cardiovascular system;

a blood pump configured to control the flow of blood through the blood lines;

an effluent fluid line connected, at one end thereof, to an outlet of the secondary chamber and, at its other end, optionally connected to a waste container;

at least two fluid lines selected in the group comprising:
- a pre-dilution infusion fluid line connected at one end thereof to the blood withdrawal line and at its other end to a first container,
- a post-dilution infusion fluid line connected at one end thereof to the blood return line and at its other end to a second container,
- a dialysis fluid line connected at one end thereof to the inlet of the secondary chamber and at its other end to a third fluid container,
- a pre-blood pump infusion line connected at one end thereof to a fourth container and at its other end to the blood withdrawal line in a region of this latter which is positioned in use upstream the blood pump,
- one or more syringe lines connected at one end thereof either to the blood withdrawal line or to the blood return line or directly to the patient, and at its other end to a syringe container;

the pump or a valve regulator being configured to regulate the flow of fluid through said fluid lines and a control unit being connected to the pump or valve regulator, wherein the process is executed by the control unit and comprises the following steps:
calculating set values of two or more of the fluid flow rates selected in the group including:
- a fluid flow rate $Q_{rep1}$ through the pre-dilution infusion fluid line,
- a fluid flow rate $Q_{rep2}$ through the post-infusion fluid line,
- a fluid flow rate $Q_{pbp}$ through the pre-blood pump infusion fluid line,
- a fluid flow rate $Q_{dial}$ through the dialysis liquid fluid line,
- a fluid flow rate $Q_{syr}$ through the syringe fluid line or lines,
- a fluid flow rate $Q_{eff}$ through the effluent fluid line, by that emptying times of at least two among the containers of fresh fluid and, optionally, the filling time of the waste container are multiple of a same reference time $T_r$, and optionally storing said calculated set values in identified retrievable memory locations for subsequent use to control said means for regulating the flow of fluid.

By defining the reference time $T_r$ and a multiplication factor, it is possible to define in relation to each fresh fluid line e.g. the following:

an emptying time of the respective container which is the same of the emptying time of a container relating to another line, an emptying time of the respective container which is the multiple of the emptying time of a container relating to another line, an emptying time of the respective container which is a fraction (A/B where both A and B are integers) of the emptying time of a container relating to another line.

Optionally the above relations may be made with the filling time of the waste container.

In a 90$^{th}$ aspect according to the one of the preceding two aspects, the apparatus comprises at least the following three fluid lines:
- a pre-dilution infusion fluid line connected to the blood withdrawal line,
- a post-dilution infusion fluid line connected to the blood return line,
- a dialysis fluid line connected to the inlet of the secondary chamber;

and wherein the process comprises the following further steps:

allowing selection by an operator of at least one set value for a parameter selected in the group comprising:
a treatment time T, a dose $D_{set}$ of the treatment to be delivered to the patient, a fluid flow rate $Q_{rep1}$ through the pre-dilution infusion fluid line, a fluid flow rate $Q_{rep2}$ through the post-infusion fluid line, a fluid flow rate $Q_{pbp}$ through the pre-blood pump infusion fluid line, a fluid flow rate $Q_{dial}$ through the dialysis liquid fluid line, a fluid flow rate $Q_{eff}$ through the effluent fluid line, a fluid removal rate $Q_{pfr}$ from the patient, determining the weight or volume $W_i$, $V_i$ of the respective container at the beginning of the treatment or at a prefixed checkpoint or responsive to an operator's input, calculating the set value for the fluid flow rate through each of the above-listed fluid lines by imposing that emptying times of at least two among the containers of fresh fluid and, optionally, the filling time of the waste container are multiple of a same reference time $T_r$.

In a $91^{st}$ aspect according to the preceding aspect, the emptying time of each given of said first, second, third and fourth containers and/or the filling time of the waste container is substantially the same as, or multiple of, the emptying time of one or more other of said first, second, third and fourth containers, said set value for the fluid flow rate through each of the above-listed three fluid lines being calculated dividing said weight or volume $W_i$, $V_i$ of the respective container by the value of reference time $T_r$.

In a $92^{nd}$ aspect according to the one of the preceding aspects from $87^{th}$ to $91^{st}$, the calculation of reference time $T_r$ may be made as disclosed in connection with the above apparatus aspects.

In a $93^{rd}$ aspect according to the one of the preceding aspects from $87^{th}$ to $92^{nd}$ the process comprises to:

receive an initial weight or volume $W_i$, $V_i$ of one or more of said containers, receive proposed values $Q_i$ of the flow rates for said fluid lines;

receive the value of an adjustment parameter A defined as maximum relative change allowed on container change periods;

calculate the set values of said fluid flow rates $Q_{iset}$ based on the proposed values $Q_i$ the initial weight or volume $W_i$, $V_i$ of each container and the value of the adjustment parameter A.

In a $94^{th}$ aspect according to the preceding aspect the process comprises to:

receive an initial weight or volume $W_i$, $V_i$ of one or more of said containers, receive proposed values Q of the flow rates for said fluid lines, which may be either entered by the user or come from a previous calculation step, e.g. using the mathematical relations mentioned in some of the above aspects, for each pair of lines and respective containers, generate ratios of interest $R0_k$, which are reference ratios between change periods of pairs of containers and are defined for each pair of lines and respective containers, K being an integer from 1 to M, with the value of M pre-stored in the control unit memory or receivable from a user input;

calculate the containers change periods $T_i=V_i/Q_i$ or $T_i=W_i/Q_i$ and rank each circuit according to the calculated container change period, where i=1 to N with $T_i$ increasing with i;

compute all period ratios $R_{ij}=T_i/T_j$, with i>j;

compare each period ratio $R_{ij}$ to the ratios of interest $R0_k$;

verify if there is a k value verifying that $R_{ij}/R0_k$ stays within a tolerance limit (selectable by the user or preset in a memory of the computer unit), compute the number of daily saved container changes and selecting the ratios $R_{ij}$ providing the largest number of saved container changes and respecting the above tolerance limit;

apply the ratios of interest corresponding to the selected ratios $R_{ij}$ to compute the optimized flow rates $Q_{iset}$.

In a $95^{th}$ aspect according to the $93_{rd}$ aspect the process comprises to:

receive an initial weight or volume $W_i$, $V_i$ of one or more of said containers, receive proposed values Q of the flow rates for said fluid lines, which may be either entered by the user or come from a previous calculation step, e.g. using the mathematical relations mentioned in some of the above aspects, for each pair of lines and respective containers, generate ratios of interest $R0_k$, which are reference ratios between change periods of pairs of containers and are defined for each pair of lines and respective containers, K being an integer from 1 to M, with the value of M pre-stored in the control unit memory or receivable from a user input;

calculate the containers change periods $T_i=V_i/Q_i$ or $T_i=W_i/Q_i$ and rank each circuit according to the calculated container change period, where i=1 to N with $T_i$ increasing with i;

compute all period ratios $R_{ij}=T_i/T_j$, with i>j;

compare each period ratio $R_{ij}$ to the ratios of interest $R0_k$;

for each ratio $R_{ij}$ where a k value exists verifying the tolerance relation: $(1-A) \cdot R0_k < R_{ij} < (1+A) \cdot R0_k$, compute the number of daily saved container changes;

select the ratios $R_{ij}$ providing the largest number of saved container changes;

apply the ratios of interest corresponding to the selected ratios to compute the optimized flow rates $Q_{iset}$.

A $96^{th}$ aspect concerns a process of setting up a medical apparatus for the delivery or collection of fluid, the apparatus comprising:

a filtration unit having a primary chamber and a secondary chamber separated by a semi-permeable membrane;

a blood withdrawal line connected to an inlet of the primary chamber, and a blood return line connected to an outlet of the primary chamber said blood lines being designed to be connected to a patient cardiovascular system;

a blood pump configured to control the flow of blood through the blood lines;

an effluent fluid line connected to an outlet of the secondary chamber;

at least two fluid lines selected in the group comprising:
a pre-dilution infusion fluid line connected to the blood withdrawal line,
a pre-blood pump infusion line connected to the blood withdrawal line in a region of this latter which is positioned in use upstream the blood pump
a post-dilution infusion fluid line connected to the blood return line,
a dialysis fluid line connected to the inlet of the secondary chamber;

means for regulating the flow of fluid through said fluid lines;

a control unit connected to the means for regulating,
the method comprising the following steps executable by the control unit:
allow entry by an operator of the set value for at least a first fluid flow rate selected in the group including:
a fluid flow rate $Q_{eff}$ through the effluent fluid line,
a fluid flow rate $Q_{rep1}$ through the pre-dilution infusion fluid line,
a fluid flow rate $Q_{rep2}$ through the post-infusion fluid line,
a fluid flow rate $Q_{pbp}$ through the pre-blood pump infusion fluid line,
a fluid flow rate $Q_{dial}$ through the dialysis liquid fluid line, and
a fluid removal rate $Q_{pfr}$ from the patient,
allow entry of a set value for a prescribed dose $D_{set}$ to be delivered,
calculate set values of at least a second and a third of the fluid flow rates of said group of flow rates, based on the said first fluid flow rate set by the operator and on said prescribed dose value $D_{set}$ by applying said prescribed dose value $D_{set}$ and the set value of the first fluid flow rate entered by the operator to mathematical relations stored in a memory connected to the control unit.

In a 97$^{th}$ aspect according to the 96$^{th}$ said means for regulating the flow of fluid are controlled based on said set values of the fluid flow rates.

In a 98$^{th}$ aspect according to any one of the preceding two aspects, said mathematical relations stored in said memory comprise one or more of the following:
a convection-diffusion relation, relating the total fluid flow rate through said infusion fluid lines $Q_{rep1}+Q_{rep2}+Q_{pbp}$ with the fluid flow rate through said dialysis fluid line $Q_{dial}$,
a blood pre-dilution relation, relating the flow rate of blood or of plasma $Q_{BLOOD}$, $Q_{PLASMA}$ and the fluid flow rate infused in the blood withdrawal line $Q_{rep1}+Q_{pbp}$ through said pre-dilution infusion fluid line and through said pre-blood pump infusion line,
a pre-post relation, relating the fluid flow rates $Q_{rep1}+Q_{pbp}$ through pre-dilution infusion fluid line and pre-blood pump infusion line with the fluid flow rate through the post-dilution infusion line $Q_{rep2}$.

In a 99$^{th}$ aspect according to any one of the preceding three aspects the process comprises selecting at least two of said relations and calculating the set values of at least the second and third of said fluid flow rates by applying the set value of the prescribed dose and the set value of the first fluid flow rate entered by the operator to the selected mathematical relations.

In a 100$^{th}$ aspect according to any one of the preceding four aspects, the convection-diffusion relation defines a first ratio $R_1$ dividing the total fluid flow rate $Q_{rep1}+Q_{rep2}+Q_{pbp}$ through said infusion fluid lines by the fluid flow rate $Q_{dial}$ through said dialysis fluid line,
the blood pre-dilution relation defines a second ratio $R_2$ dividing the flow rate of blood or of plasma $Q_{BLOOD}$, $Q_{PLASMA}$ by the sum of fluid flow rates $Q_{rep1}+Q_{pbp}$ infused in the blood withdrawal line through said pre-dilution infusion fluid line and through said pre-blood pump infusion line, and the pre-post relation defines a third ratio $R_3$ dividing the sum of the fluid flow rates $Q_{rep1}+Q_{pbp}$ through said pre-blood pump infusion line and pre-dilution infusion line by the fluid flow rate $Q_{rep2}$ through said post-dilution infusion line.

In a 101$^{st}$ aspect according to any one of the preceding five aspects the process may include selection of optimization relations as disclosed in connection with the above apparatus aspects.

In a 102$^{nd}$ aspect according to any one of the preceding apparatus aspects, the apparatus comprises one or more scales weighing one or more of said containers, optionally wherein a corresponding scale is provided for each respective of said containers, said scales being connected to the control unit and sending to the control unit corresponding weight signals, wherein the control unit is configured to receiving the initial weight $W_i$ of one or more of said containers from one or more of said scales.

In a 103$^{rd}$ aspect a data carrier is provided comprising instructions which when executed by the control unit of an apparatus according to any one of the preceding apparatus aspects render said control unit configured to execute the respective steps described in the preceding aspects.

DESCRIPTION OF THE DRAWINGS

Aspects of the invention are shown in the attached drawings, which are provided by way of non-limiting example, wherein.

DETAILED DESCRIPTION

Figure 1A:
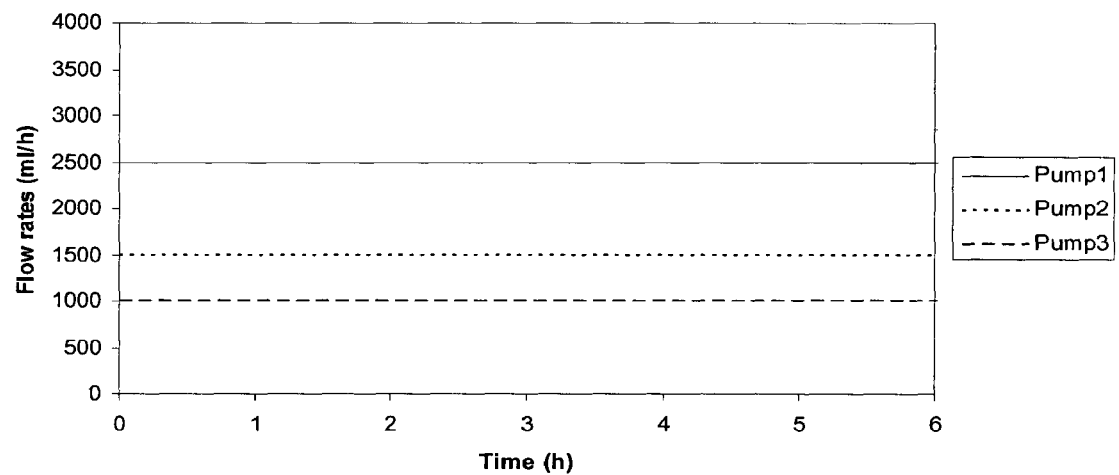
FIG. 1A shows a chart, relative to the emptying profiles of bags in accordance with a state of the art solution; the vertical axis represents the weight of each one of three bags and the horizontal axis represents the emptying time.

FIGS. 4-7 show exemplifying embodiments of apparatus for extracorporeal treatment of blood according to aspects of the invention. Note that same components are identified by same reference numerals in the figures. Also note that— although the present invention is described with specific reference to blood treatment apparatuses—the invention may also refer to apparatuses for handling a plurality of medical fluids, such as nutrients, replacement solutions, serum, or other fluids which need to be controllably injected into or withdrawn from a patient's body.

Figure 1B:
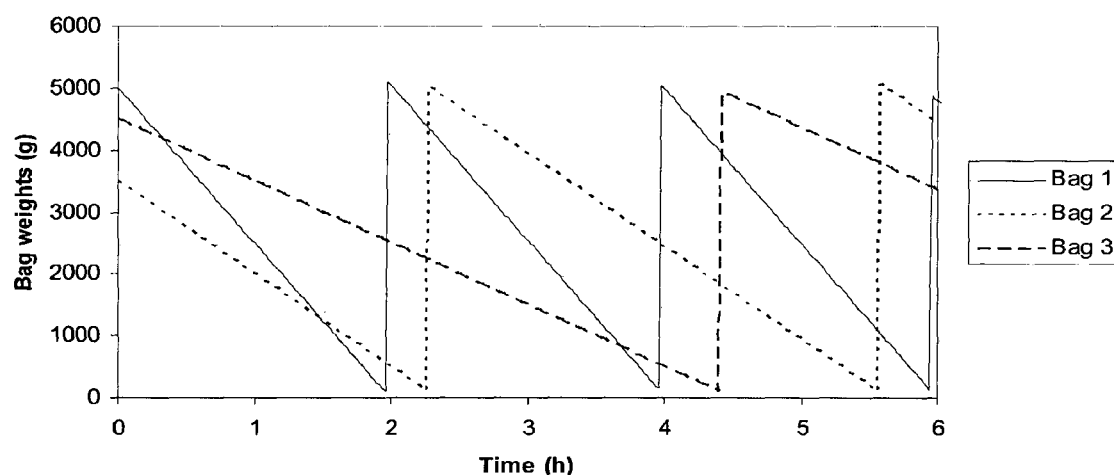
FIG. 1B shows a chart, relative to the set flow rates as a function of time for the three pumps withdrawing fluid from respective bags in order obtain the emptying profiles shown in FIG. 1A.
Figure 4:
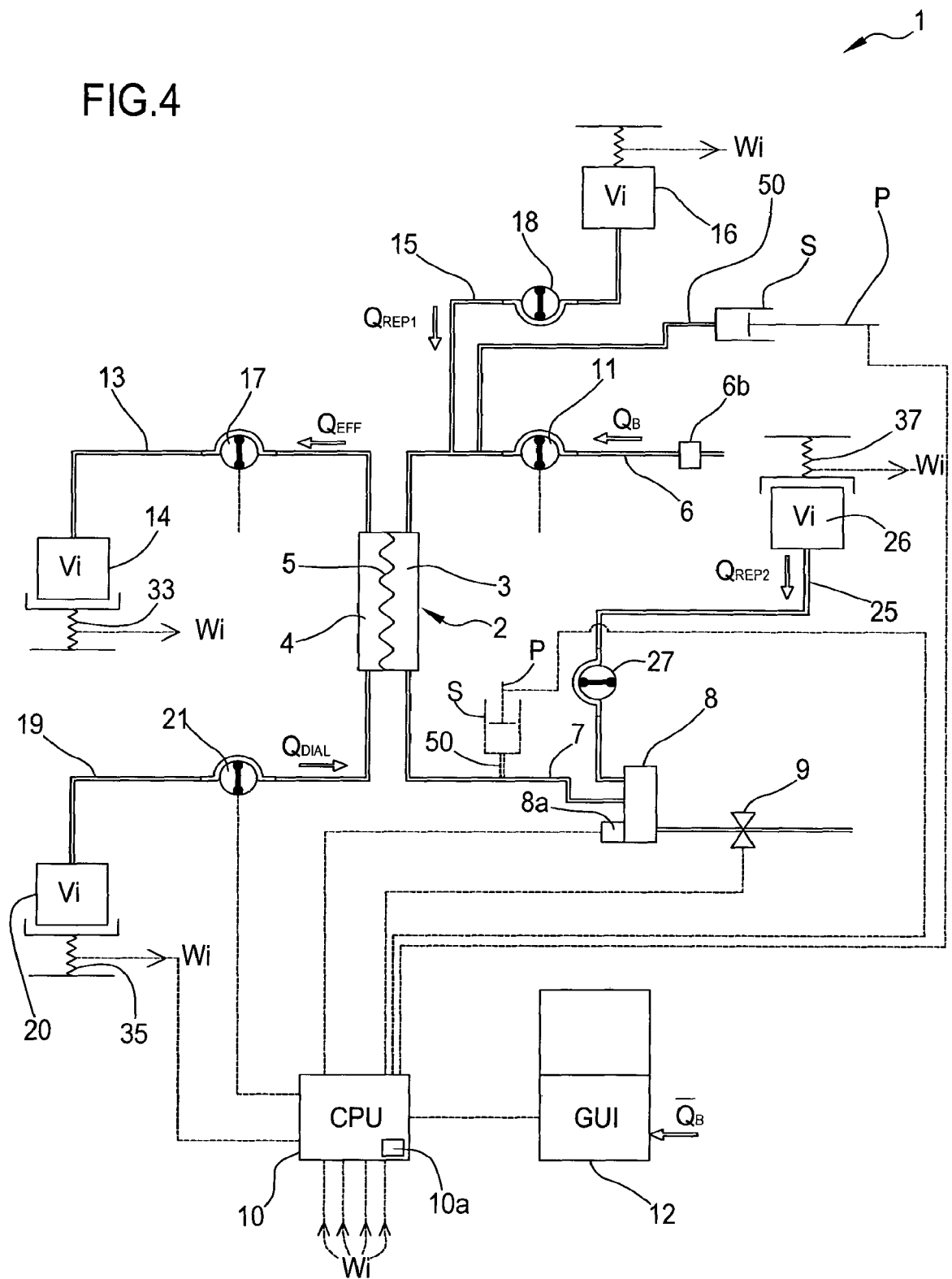
FIGS. 4-7 show schematic representations of blood treatment apparatuses according to aspects of the invention.

FIG. 4 shows an extracorporeal blood treatment apparatus 1 which is designed for delivering any one of treatments like hemodialysis, hemofiltration, hemodiafiltration, ultrafiltration. The apparatus 1 comprises a filtration unit 2 having a primary chamber 3 and a secondary chamber 4 separated by a semi-permeable membrane 5; depending upon the treatment the membrane of the filtration unit may be selected to have different properties and performances. A blood withdrawal line 6 is connected to an inlet of the primary chamber 3, and a blood return line 7 is connected to an outlet of the primary chamber 3. In use, the blood withdrawal line 6 and the blood return line 7 are connected to a needle or to a catheter or an implanted port or other access device (not shown) which is then placed in fluid communication with the patient vascular system, such that blood may be withdrawn through the blood withdrawal line, flowed through the primary chamber and then returned to the patient's vascular system through the blood return line. An air separator, such as a bubble trap 8, may be present on the blood return line; moreover, a safety clamp 9 controlled by a control unit 10 may be present on the blood return line downstream the bubble trap 8. A bubble sensor 8a, for instance associated to the bubble trap 8 or coupled to a portion of the line 7 between bubble trap 8 and clamp 9 may be present: if present, the bubble sensor is connected to the control unit 10 and sends to the control unit signals for the control unit to cause closure of the clamp 9 in case one or more bubbles are detected. As shown in FIG. 1, the blood flow through the blood lines is controlled by a blood pump 11, for instance a peristaltic blood pump, acting either on the blood withdrawal line (as shown e.g. in FIG. 1) or on the blood return line. An operator may enter a set value for the blood flow rate $Q_{BLOOD}$ through a user interface 12 and the control unit 10, during treatment, is configured to control the blood pump based on the set blood flow rate. Note that, alternatively, the blood pump 11 may be automatically controlled with no need of user input: in that case control unit may control the blood pump at a prefixed flow rate or at a flow rate calculated based on other parameters such as, for instance, pressure detected upstream the blood pump; if the blood pump 11 is controlled based on the pressure signal detected upstream the blood pump then a pressure sensor 6b is present in the tract 6a of bloodline upstream the blood pump 11: for instance the control unit 10 may be designed to drive the blood pump in a manner to keep the pressure detected by pressure sensor 6b within a prefixed range, or below a prefixed threshold. Going back to FIG. 4, an effluent fluid line 13 is connected, at one end, to an outlet of the secondary chamber 4 and, at another end, to an effluent fluid container 14 collecting the fluid extracted from the secondary chamber. The embodiment of FIG. 1 also presents a pre-dilution fluid line 15 connected to the blood withdrawal line: this line 15 supplies replacement fluid from an infusion fluid container 16 connected at one end of the pre-dilution fluid line. Note that a post-dilution fluid line 25 may also be present connecting an infusion fluid container 26 to the blood return line, for instance in correspondence of bubble trap 8. When the apparatus (as in FIG. 4) includes both a pre-dilution 15 and a post infusion fluid line 25 each infusion fluid line may be connected to a respective infusion fluid container or the two infusion fluid lines could receive infusion fluid from a same infusion fluid container or other fluid source. An effluent fluid pump 17 operates on the effluent fluid line under the control of said control unit 10 to regulate the flow rate $Q_{eff}$ across the effluent fluid line. Furthermore, an infusion pump 18 operates on the infusion line 15 to regulate the flow rate $Q_{rep1}$ through the pre-dilution fluid line 15. Note that in case of two infusion fluid lines (pre-dilution and post-dilution) each fluid line 15, 25 may cooperate with a respective infusion pump 18, 27 to regulate the flow rate $Q_{rep1}$ and $Q_{rep2}$ through the respective lines. The apparatus of FIG. 4, further includes a dialysis fluid line 19 connected at one end with a dialysis fluid container 20 and at its other end with the inlet of the secondary chamber 4 of the filtration unit. A dialysis pump 21 works on the dialysis fluid line 19 under the control of said control unit 10, to supply fluid from the dialysis liquid container to the secondary chamber at a flow rate $Q_{dial}$.

The dialysis fluid pump 21, the infusion fluid pump 18 (or pumps 18, 27) and the effluent fluid pump 17 are part of means for regulating the flow of fluid through the respective lines and, as mentioned, are operatively connected to the control unit 10 which controls the pumps as it will be in detail disclosed herein below. The control unit 10 is also connected to a memory 10a and to user interface 12, for instance a graphic user interface, which receives operator's inputs and displays the apparatus outputs. For instance, the graphic user interface 12 may include a touch screen, a display screen and/or hard keys for entering user's inputs or a combination thereof.

Figure 5:
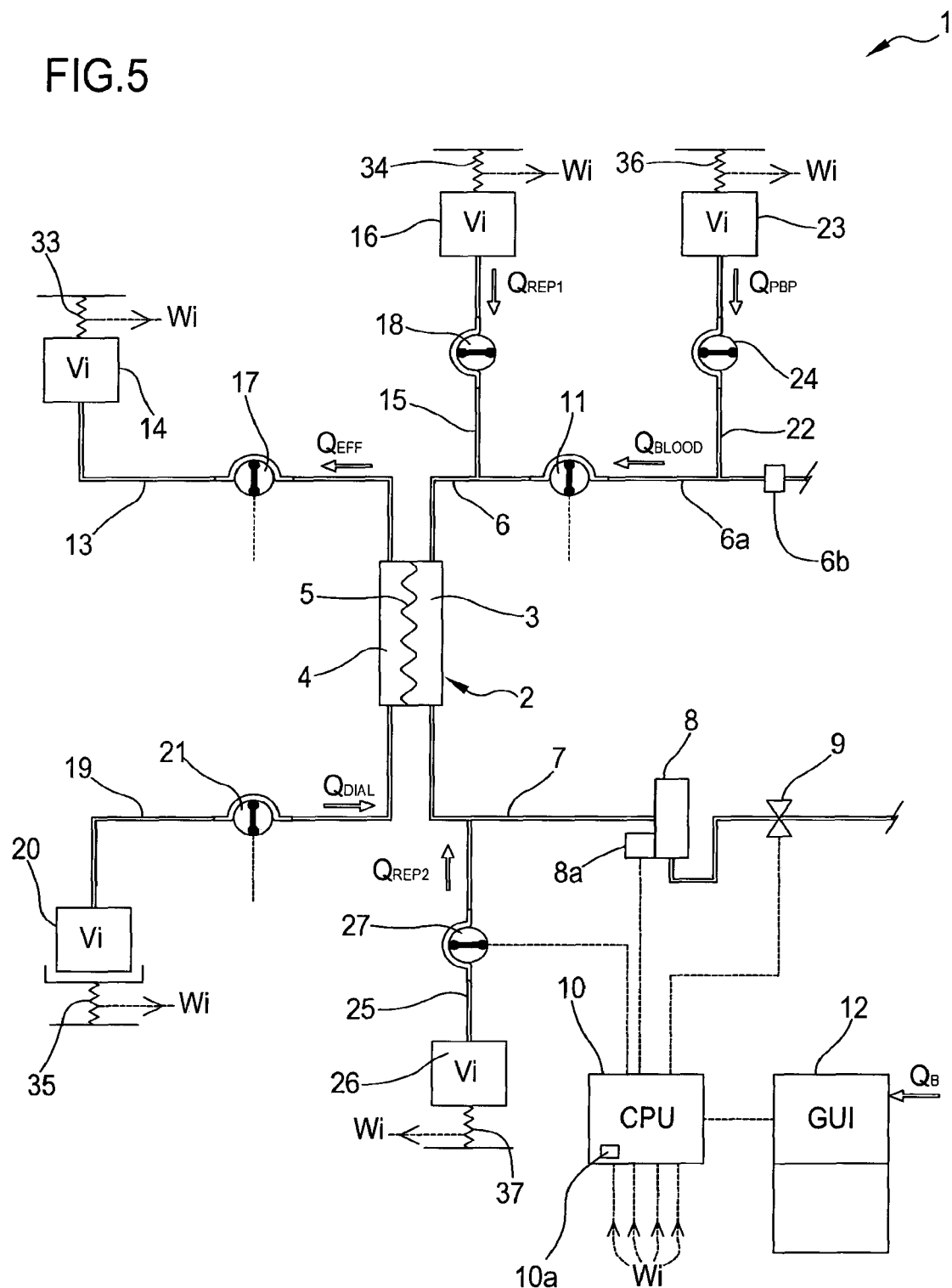

The embodiment of FIG. 5 shows an alternative apparatus 1 where the same components described for the embodiment of FIG. 1 are also present and are identified by same reference numerals and thus not described again. Additionally, the apparatus 1 shown in FIG. 2 presents a further infusion line connected, at one end, with a tract 6a of the blood withdrawal line 6 positioned upstream the blood pump 11 and, at its other end, with a further infusion fluid container 23, which for instance may contain a drug, or a regional anticoagulant such as a citrate solution, or a nutrients solution or other. This further infusion line is herein referred to as pre-blood pump infusion line 22. The means for regulating comprises a pump 24, for instance a peristaltic pump controlled by control unit 10, acting on a segment of the pre-blood pump infusion line to regulate a pre-blood pump infusion rate $Q_{pbp}$. The apparatus of FIG. 5 may also present a post-dilution line 25 similar to that of the apparatus of FIG. 4: the infusion line 25 in FIG. 2 is connected to the blood return line 7 in a location between the bubble trap 8 and the exit of the filtering unit 2; alternatively the infusion line may be directly connected to bubble trap 8.

Figure 6:
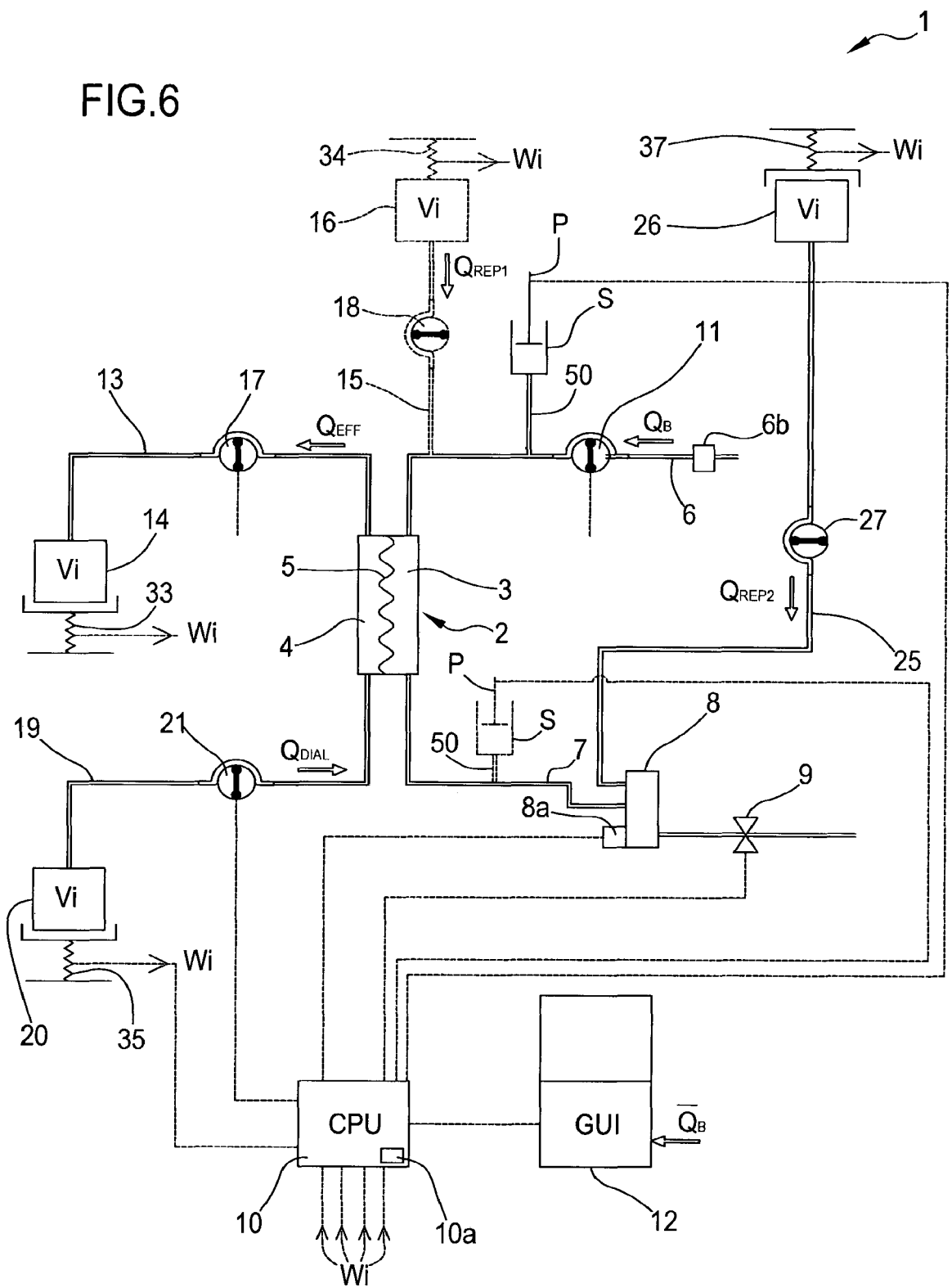

The apparatus of FIG. 6 is similar to that of FIG. 4 but includes only either the post-dilution line 25 with its pump 27 and infusion fluid container 26 or the pre-dilution line 15 with its pump and container (see phantom line).

Figure 7:
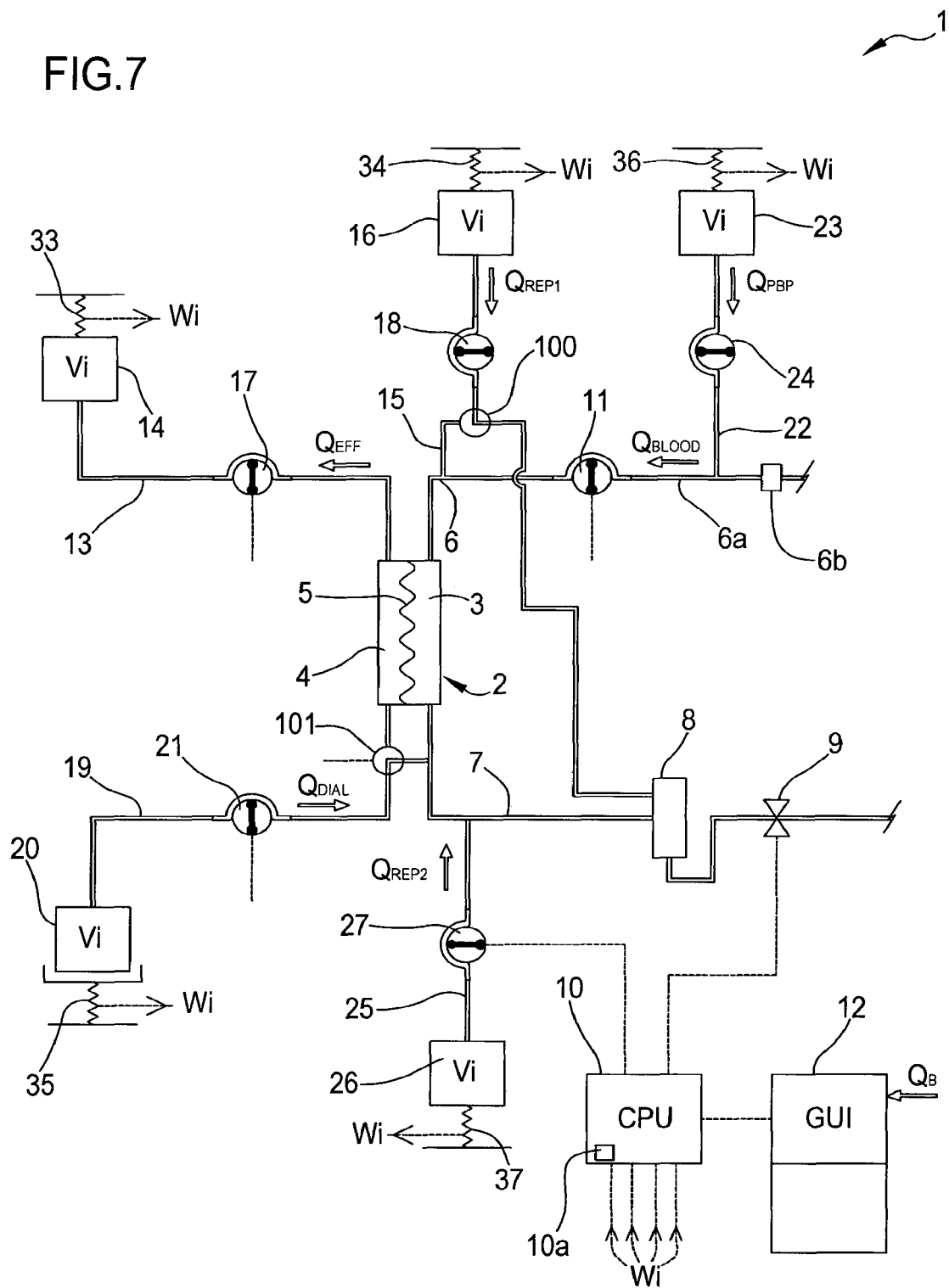

A further embodiment is shown in FIG. 7. In this embodiment, compared to that of FIG. 5, a line switch 101 operates (such as a 3-way valve or a clamp mechanism) on the dialysis fluid line 19 which allows the dialysis line to be selectively coupled either to the inlet of the second chamber 4 or to the return line 7: in this latter case the dialysis line would work as a post-dilution line. Moreover, a further line switch 100 operates on the infusion line 15 which allows the infusion line 15 to be selectively coupled either to the blood withdrawal line or to the blood return line. A further post-dilution line 27 may or may not be present.

Of course the above described blood treatment apparatus are of exemplifying character only and further variants may be envisaged without departing from the scope of the invention.

For instance, the above apparatuses may also include a syringe pump provided with a container S connected via a respective line to one of the blood lines 6 and 7 and with a plunger P for displacing the fluid in the container. In FIGS. 4 and 6 the syringe pump is connected via syringe line 50 to the blood withdrawal line 6, downstream the blood pump. Syringe line 50 may be used to inject medicaments, anticoagulants or other fluids. Although not shown, also the circuits shown in FIGS. 5 and 7 may include a syringe line 50 with respective container S and plunger P connected either to the blood withdrawal line and/or to the blood return line.

The means for regulating have been described as one or more pumps (in particular of the peristaltic type); however it is not to be excluded that other flow regulating means such as valves or combinations of pumps and valves may be used. Moreover, in case of syringe lines, the plunger P acts as a flow regulating means.

Dose Definitions

In the present specification, dose refers to a flow rate or to a combination of flow rates.

For example, one of the following magnitudes may be used as dose:

effluent dose $D_{eff}$: the flow rate across the effluent line $Q_{eff}$, convective dose $D_{conv}$: the sum of the flow rates $Q_{rep}+Q_{pbp}+Q_{pfr}$, where $Q_{pfr}$ represents the patient fluid removal rate, $Q_{rep}$ is the flow rate through the infusion line or lines (e.g. $Q_{rep1}+Q_{rep2}$) connected directly to the patient or connected to the blood circuit downstream the blood pump and $Q_{pbp}$ is the flow rate through the pre-blood pump infusion line, diffusive dose $D_{dial}$: the flow rate $Q_{dial}$ of fluid supplied to the filtration unit secondary chamber.

urea dose $D_{urea}$: estimated urea clearance; note that a first approximated expression assumes that filter Urea clearance is more or less identical to effluent flow rate $Q_{eff}$; alternatively a urea monitor could be placed on the effluent line in order to measure an actual value of the urea clearance; in a further alternative, an estimate of urea clearance more accurate than $Q_{eff}$ especially when operating with large flow rates or small filters (paediatric conditions), may be provided by the following equations:

a) For purely diffusive mode (where there is no infusion of replacement fluid and where the patient fluid removal rate is zero or substantially zero) and counter-courant flow configuration (fluids in the chambers of the filtration unit 2 are countercurrent):

$$Z = \frac{Qpw_{inlet}}{Qdial}$$

$$NT = \frac{S/RT}{Qpw_{inlet}}$$

$$K(Qpw_{inlet}, Qdial) = Qpw_{inlet} \times \frac{\exp[NT \times (1-Z)] - 1}{\exp[NT \times (1-Z)] - Z} \text{ if } Z \neq 1$$

$$K(Qpw_{inlet}, Qdial) = Qpw_{inlet} \times \frac{NT}{NT+1} \text{ if } Z = 1$$

where: S (effective surface area) is dependent on the hemodialyzer (as filtration unit 2) in use; RT is total mass transfer resistance dependent of the hemodialyzer in use (membrane properties, filter design) and the solute of interest, in this case urea; and $Qpw_{inlet}$ is the plasma water flow rate at the inlet of the filtration unit 2.

b) In case of presence of both $Q_{dial}$ of one or more infusions of fluid, then:

$$\gamma = \exp\left(\frac{SC \times Qfil}{S/RT}\right) - 1$$

$$f = \left(\frac{Qpw_{inlet} - SC \times Qfil}{Qpw_{inlet}} \times \frac{Qdial + SC \times Qfil}{Qdial}\right)^{1/\gamma}$$

$$K(Qpw_{inlet}, Qdial, Qfil) = \frac{Qpw_{inlet} \times Qdial - f \times (Qpw_{inlet} - SC \times Qfil) \times (Qdial + SC \times Qfil)}{Qdial - f \times (Qpw_{inlet} - SC \times Qfil)}$$

where: S (effective surface area) is dependent on the hemodialyzer in use; $Q_{fil}=Q_{pbp}+Q_{rep}+Q_{pfr}$ (again, $Q_{pfr}$ represents the patient fluid removal rate, $Q_{rep}$ is the flow rate through the infusion line or lines connected directly to the patient or connected to the blood circuit downstream the blood pump and $Q_{pbp}$ is the flow rate through the pre-blood pump infusion line); and $Qpw_{inlet}$ is the plasma water flow rate at the inlet of the filtration unit 2.

clearance dose: an estimated clearance for a given solute; for certain solutes a first approximated expression assumes that filter solute clearance is more or less identical to effluent flow rate $Q_{eff}$; alternatively solute clearance may be estimated as function of all flow settings and of dialyzer/filter related parameters; alternatively appropriate sensors could be placed to measure conductivity or concentration and thereby allow calculation of an actual clearance for a given solute (e.g. sodium), for instance using one of the methods described in EP patent n. 0547025 or EP patent n. 0658352 or EP patent n. 0920887, the specification of all of which is herein incorporated by reference. In a further alternative the equations of above paragraphs a) and b) as described for the urea clearance could be used with RT and SC adapted to take into account the specific solute.

In the course of the following description reference will be made to the above dose definitions which are relating to doses not normalized to patient body weight (BW) or patient surface area (PA). Of course the same principles and formulas below described could be normalized to body weight or patient surface area by dividing the dose value by either body weight BW or surface area PA.

Normalized Dose=Dose/BW or $N$Dose=Dose/$PA$×1.73 (when normalised to a 1.73 m² surface area patient)

Furthermore, the above defined doses could be corrected to take into account the predilution effect, when a fluid replacement line is present upstream the treatment unit, such as lines 15 and 22 in the enclosed drawings. Each of the above defined doses could be corrected multiplying the dose value times a dilution factor $F_{dilution}$:

Dose$_{corr\_xxx}$=$F_{dilution}$×Dose$_{xxx}$ (with $xxx$=eff, conv, dial, etc)

The dilution factor $F_{dilution}$ may be defined according to one of the following:

Blood dilution factor: $Fdilution_{blood} = \dfrac{Qblood}{Qblood + Qpre}$

Plasma dilution factor: $Fdilution_{plasma} =$
$\dfrac{Qp}{Qp + Qpre} = \dfrac{(1 - Hct) \times Qblood}{(1 - Hct) \times Qblood + Qpre}$ Plasma Water dilution factor: $Fdilution_{pw} =$
$\dfrac{Qpw}{Qpw + Qpre} = \dfrac{(1 - Hct) \times Fp \times Qblood}{(1 - Hct) \times Fp \times Qblood + Qpre}$ Where $Q_{pre}$ is the total predilution infusion rate (where two infusion lines are present upstream the treatment unit, as lines 15 and 22, $Q_{pre}$ combines PBP infusion 15 and pre-replacement infusion 22)

$Q_{BLOOD}$: blood flow rate
$Q_{PLASMA}$: plasma flow rate
$Q_{pw}$: plasma water flow rate
Hct: haematocrit
$F_p$: plasma water fraction, which is a function of total protein concentration (typical value Fp=0.95)

In practice, the effluent dose corrected for the predilution effect would be: Dose$_{corr\_eff}$=$F_{dilution}$×Dose$_{eff}$.

The Control Unit

The control unit 10 is connected to the various sensors, to the means for regulating the flow rate through the various lines (in the above examples this means comprises the pumps active on the lines and the switch valves) and to the user interface. The control unit 10 may comprise a digital processor (CPU) and necessary memory (or memories), an analogical type circuit, or a combination thereof. In the course of the present description it is indicated that the control unit is "configured" or "programmed" to execute certain steps: this may be achieved in practice by any means which allow configuring or programming the control unit. For instance, in case of a control unit comprising one or more CPUs, a program may be stored in an appropriate memory containing instructions which, when executed by the control unit, cause the control unit to execute the steps herein described. Alternatively, if the control unit is of an analogical type, then the circuitry of the control unit may be designed to include circuitry configured in use to execute the steps herein disclosed.

In the example of FIG. 4, the control unit 10 may be configured to calculate set values of fluid flow rate n through the pre-dilution infusion fluid line 15, of fluid flow rate $Q_{rep2}$ through the post-infusion fluid line 25, and of fluid flow rate $Q_{dial}$ through the dialysis fluid line 27, by imposing that an emptying time of the containers of fresh fluid 16, 20, 26 is either identical to, or proportional to, or multiple of the emptying time of one of the other containers of fresh fluid. In the example of FIG. 5, the control unit 10 may be configured to calculate set values of fluid flow rate $Q_{rep1}$ through the pre-dilution infusion fluid line 15, of fluid flow rate $Q_{rep2}$ through the post-infusion fluid line 25, of fluid flow rate $Q_{dial}$ through the dialysis fluid line 27, and of $Q_{pbp}$ through line 22 by imposing that an emptying time of the containers of fresh fluid 16, 20, 23, 26 is either identical to or multiple of or proportional to the emptying time of one of the other containers of fresh fluid. In the example of FIG. 6, the control unit 10 may be configured to calculate set values of fluid flow rate $Q_{rep2}$ through the post-infusion fluid line 25, of fluid flow rate n through the dialysis fluid line 27 by imposing that an emptying time of one of the containers of fresh fluid 20, 26 is either identical to or multiple of or proportional to the emptying time of the other container of fresh fluid 26, 20. Finally, in the example of FIG. 7, the control unit 10 may be configured to calculate set values of fluid flow rate $Q_{rep1}$ through the pre-dilution infusion fluid line 15, of fluid flow rate $Q_{dial}$ through the dialysis fluid line 27, and of $Q_{pbp}$ through line 22 by imposing that an emptying time of the containers of fresh fluid 16, 20, 23 is either identical to or proportional to or multiple of the emptying time of one of the other containers of fresh fluid. In other words, the control unit may be configured to calculate the set flow rates through the various lines of fresh fluid such as to either synchronize the emptying time of all containers (e.g. bags) or to make sure that the emptying time of each container is a multiple of a reference emptying time so that the frequency of bag/container substitutions is minimized or at least reduced. In a further aspect which may be combined to the above synchronization criteria, the control unit may also be configured to calculate the set value of the fluid flow rate $Q_{eff}$ through the effluent fluid line 13, by imposing that the filling time of the waste container 14 is substantially same as, proportional to, or multiple of the emptying time of one or more of the other containers of fresh fluid.

In accordance with an alternative aspect, which is of interest for example when the fluid flow rate through the effluent line is fixed by other conditions, the control unit may calculate a set value ($N_{eff\text{-}change}$) of the waste container volume or weight at which the control unit considers that the waste container is full (which is basically a calculated threshold as opposed to a prefixed threshold): this set value ($N_{eff\text{-}change}$) may be calculated by imposing that the filling time of the waste container 14 is substantially same as, proportional to, or multiple of the emptying time of one or more of the other containers of fresh fluid. When reached the set value ($N_{eff\text{-}change}$) the control unit is configured to trigger a signal, e.g. to user interface, requesting a waste container change. Note that this alternative solution may add significant synchronization in bag changes while normally losing little volume in the waste container (namely while only shortly anticipating the waste container change).

Once the set values have been calculated the control unit may be configured to ask, or wait, for a confirmation which may be entered by the user, e.g. through action onto the user interface 12. The control unit is designed to control the means for regulating the flow rate based on the calculated set values either automatically (i.e. with no need of any action on the part of an operator), or after the appropriate confirmation is entered and a confirmation signal received at the control unit.

Figure 2A:
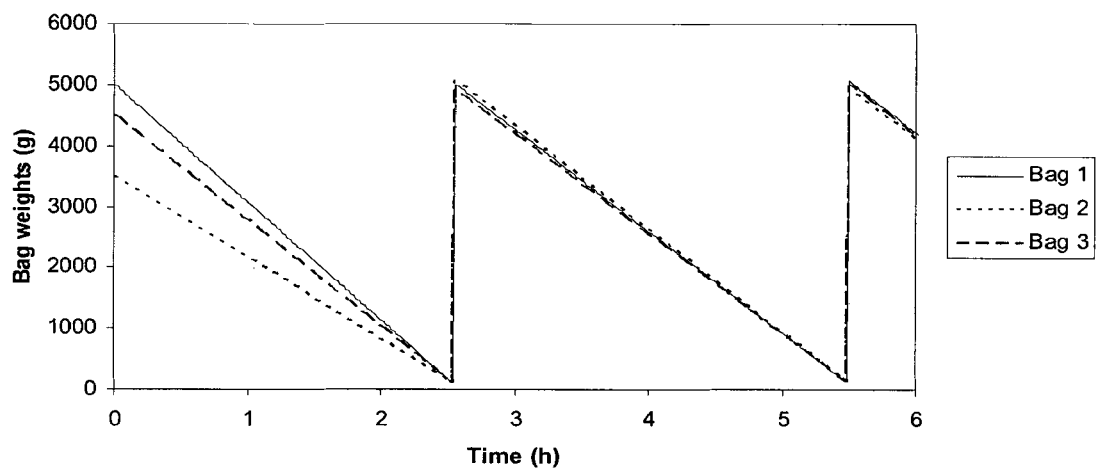
FIG. 2A shows a chart, relative to the emptying profiles of bags in accordance with aspects of the invention, where the vertical axis represents the weight of each one of three bags and the horizontal axis represents the emptying time.
Figure 2B:
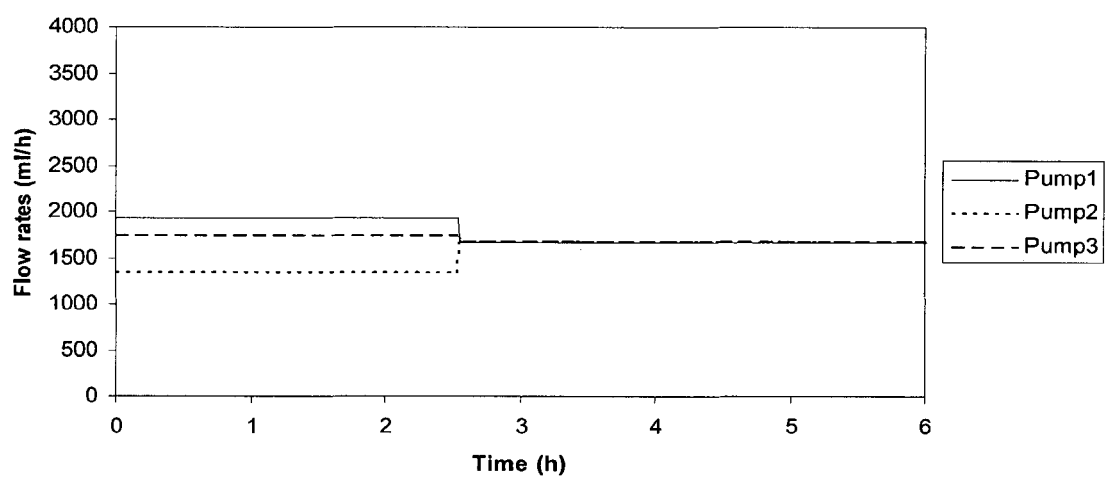
FIG. 2B shows a chart, relative to the set flow rates as function of time for the three pumps withdrawing fluid from respective bags in order obtain the emptying profiles shown in FIG. 2A; as it may be seen although the initial weight of each bag is different all bags are emptied at the same time thus minimizing the number of times the equipment must be stopped for proceeding with bag substitution.
Figure 3A:
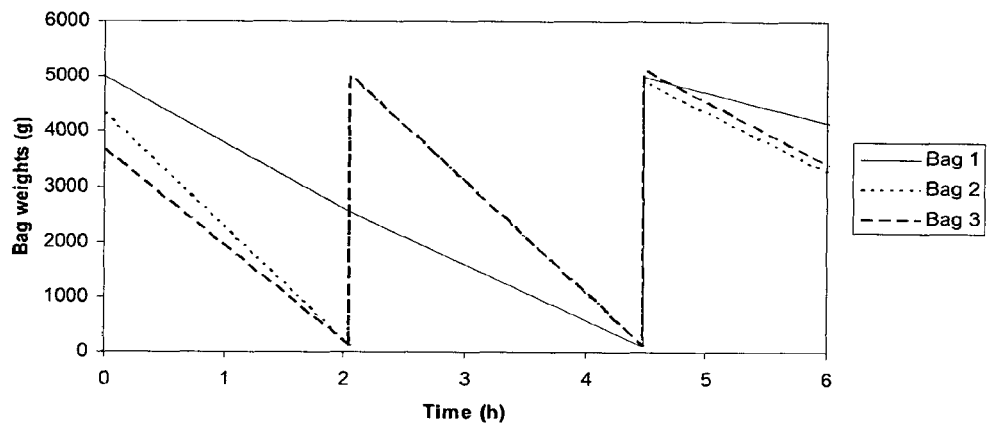
FIG. 3A shows a chart, relative to the emptying profiles of bags in accordance with aspects of the invention, where the vertical axis represents the weight of each one of three bags and the horizontal axis represents the emptying time diagram of a blood treatment apparatus according to one aspect of the invention.
Figure 3B:
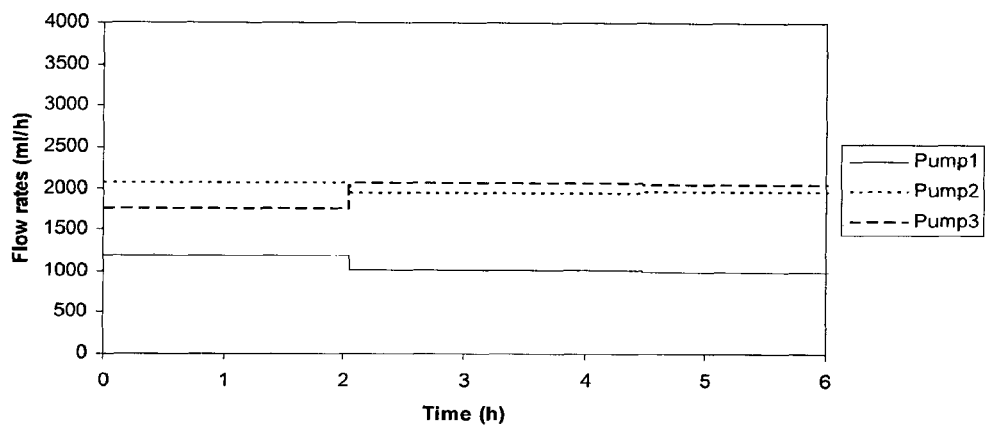
FIG. 3B shows a chart, relative to the set flow rates as a function of time for the three pumps withdrawing fluid from respective bags in order obtain the emptying profiles shown in FIG. 3A.

The control unit 10 may be configured to store, e.g. in a memory connected to the same control unit, the maximum volume of fluid which may be contained in each container of fresh fluid. The control unit may also be configured to store in a memory connected to the same control unit the maximum volume of fluid which may be contained in said waste container. The volume each container may host may be detected by a sensor associated to each respective container and connected to the control unit, or may be entered by an operator for each respective container through a user interface connected to the control unit, or determined by the control unit associating an identification code (indicia such as a bar code, an RFID or other identification means may be associated to the container) on each respective container to a respective volume, or said volume may be pre-stored in said memory. By knowing the volume of fluid that may be hosted in each container, the control unit may be configured to generate an alarm signal and/or to stop the treatment when the maximum quantity of fluid in one fresh fluid container (i.e. in one among the infusion fluid containers 16, 23, 26 and the dialysis fluid container 20) is reached, corresponding to a "empty container" threshold. In this situation, the user knows that he is supposed to substitute all fresh fluid containers (if the emptying is simultaneous on all bags as shown in FIGS. 2A, 2B) or at least to substitute a known number of the fresh fluid containers (if the emptying of the bags or containers is synchronized to happen for two or more containers at prefixed intervals, as shown in FIG. 3A, 3B). The control unit may also be configured to generate an alarm signal and/or to stop the treatment when the maximum quantity of fluid has been reached in the effluent fluid container (corresponding to a "full container" threshold). By treatment stop it is meant a condition where the control unit is configured to stop at least the pumps delivering fresh fluid (namely pumps 18, 21, 24, 27, 17 in the embodiments of FIGS. 5 and 7; pumps 18, 21, 27, 17 in the embodiment of FIG. 4; pumps 21, 27, 17 or 21, 18, 17 in the embodiment of FIG. 6) and optionally also the blood pump 11.

In the examples shown a respective scale (or other force sensor) is associated to the support of each container for detecting in real time the actual weight, and thus the current volume of fluid, of each container. In this manner the control unit, which is connected to the scales, may determine when the volume of fluid in each respective container is approaching or passing the respective thresholds (empty or full) as above described. Of course alternative sensors (e.g. level sensors) depending upon the circumstances and or the structure of the containers.

Synchronization of the Emptying and/or Filling Time of the Containers.

Figure 8:
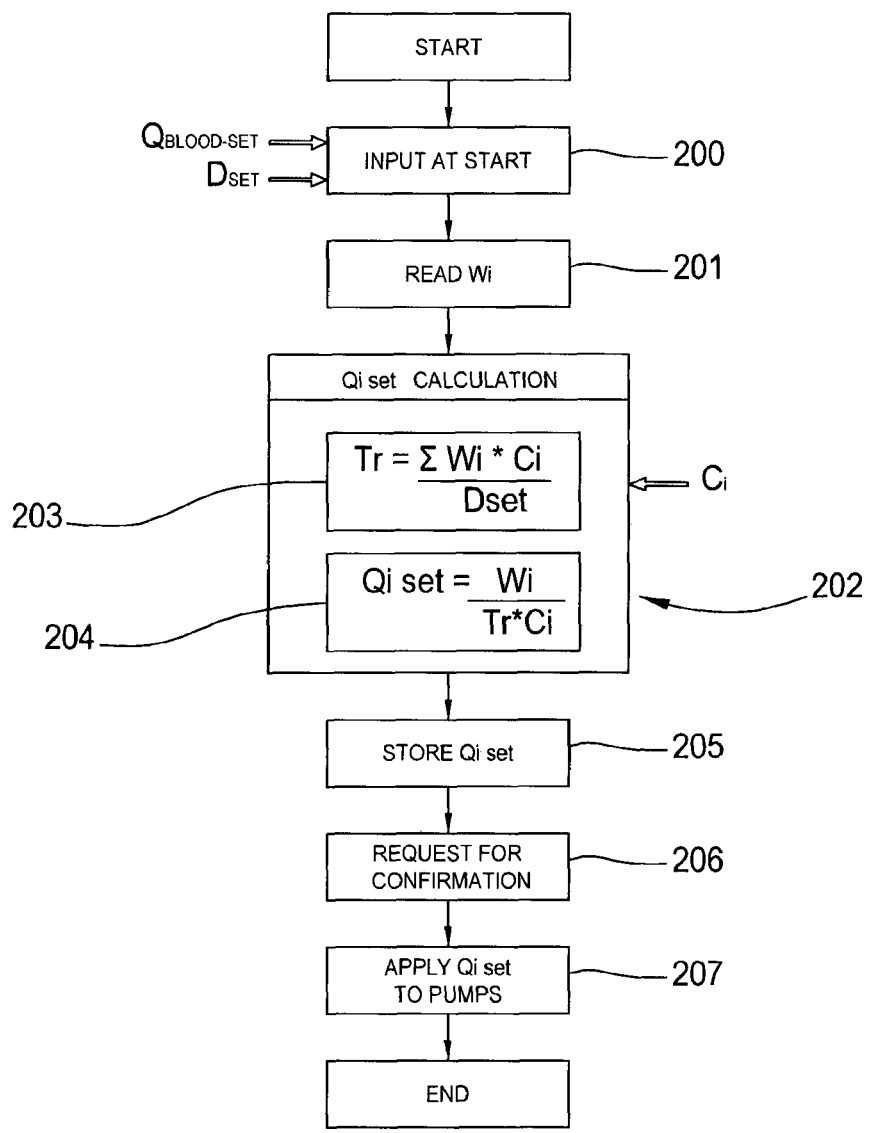
FIG. 8 is a flowchart of a process of calculating set flow rates in a medical apparatus for delivery or collection of fluids, according to an aspect of the invention.

In accordance with a first solution, see the flowchart of FIG. 8, the control unit 10 is configured to allow selection by an operator of a set value for the treatment dose $D_{set}$ to be delivered to the patient during the treatment (step 200). Alternatively, the set value of the dose may be received through an external channel or be pre-stored in a memory connected to the control unit.

This set value may be for instance an effluent dose flow rate $D_{eff\_set}$, which is the prescribed mean value of the flow rate through the effluent line, or a convective dose flow rate $D_{conv\_set}$, which is the prescribed mean value of the sum of the flow rates $Q_{rep1}$, $Q_{pbp}$, $Q_{rep2}$ through any infusion fluid line and the patient fluid removal rate $Q_{pfr}$, or a diffusive dose flow rate $D_{dial\_set}$, which is the prescribed mean value of the flow rate through the dialysis fluid line $Q_{dial}$. The control unit also receives the readings of the scales and thus knows the values $W_i$ of the initial weights of each container (step 201). Alternatively the control unit may read or know the initial volume $V_i$ of each container. In the description.

Then the set value $Q_{iset}$, namely the flow rate to be set in each fluid line is calculated (step 202). Depending upon the set value $D_{set}$ which has been entered or received, the control unit is configured to calculate a reference time value $T_r$ in different ways, namely:

- if $D_{dial\_set}$ is being set, $T_r$ is calculated by dividing the initial weight $W_i$ of the fresh dialysate container 20 by the dose flow rate $D_{dial\_set}$ of the line leading to the same container, or
- if $D_{conv\_set}$ is being set, $T_r$ is calculated by dividing the sum of the initial weights $W_i$ of the replacement fluid containers (depending upon the circuit structure those present among containers 16, 23, 26) by the dose flow rates of the lines $D_{conv\_set}$ leading to the same containers, or
- if $D_{eff\_set}$ is being set, $T_r$ is calculated by dividing the sum of the initial weights of the first, second, third, and fourth containers (depending upon the circuit structure those present among containers 16, 20, 23, 26) by the effluent dose flow rate $D_{eff\_set}$.

Once the reference time $T_r$ is calculated (step 203), the control unit is configured to determine the fluid flow rate in each one of the fresh fluid lines by dividing a weight $W_i$ of the respective container by the value of reference time $T_r$ (step 204).

For the sake of simplicity, the description given above in connection with steps 203 and 204 was restricted to the simultaneous emptying of all the bags/containers being used. In most cases this results in having all the pumps running at the same flow rate considering that all fluid bags have roughly the same initial weight. To give more flexibility to the system, it is possible to attribute a weighting factor per pump/bag in such a manner that the emptying time of a given bag could be a multiple of the emptying time of one or more bags. FIGS. 3A and 3B show a second solution where the time required for emptying one of the bags is twice that required for the other 2 bags. Thus, in general and as shown in FIG. 8, it is possible associating a multiplying weighing coefficient $c_i$ to each weight $W_i$ of the respective container when calculating the value for $T_r$. Note that the volumes $V_i$ of each of the containers may be used as an alternative to the weights also for this second solution. Moreover, note $c_i$ is an integer: when all $c_i$ values are imposed to be equal to 1 then all containers empty at the same time, while if for instance, as in FIG. 3A, one of the $c_i$ values is imposed to be equal to 2 and the others equal to 1, then two bags empty twice as faster than the other. In general $c_i$ (normally equal to 1, 2, 3, or 4 or 5) may be used to customize the control by allowing the emptying times of the various bags to be one multiple of one the remaining bags. In this case $T_r$ would be calculated as follows:

$$T_r = (\Sigma W_i \cdot c_i)/\text{Dose}$$

$Q_{iset}$, namely the flow rate to be set in each fluid line, is then computed also taking the value of each coefficient $c_i$ into account as:

$$Q_{iset} = W_i/(T_r \cdot c_i)$$

Once the $Q_{iset}$ values are calculated, following one or the other of the above sequence of steps, they are stored in a memory (step 205) and then applied to control the pump speeds as described herein below in greater detail with reference to certain embodiments (step 207). In accordance with an optional aspect the control unit may issue a signal to the user interface 12 requesting a confirmation (206) from the user before actually applying the calculated values of $Q_{iset}$ to control the pumps.

Figure 9:
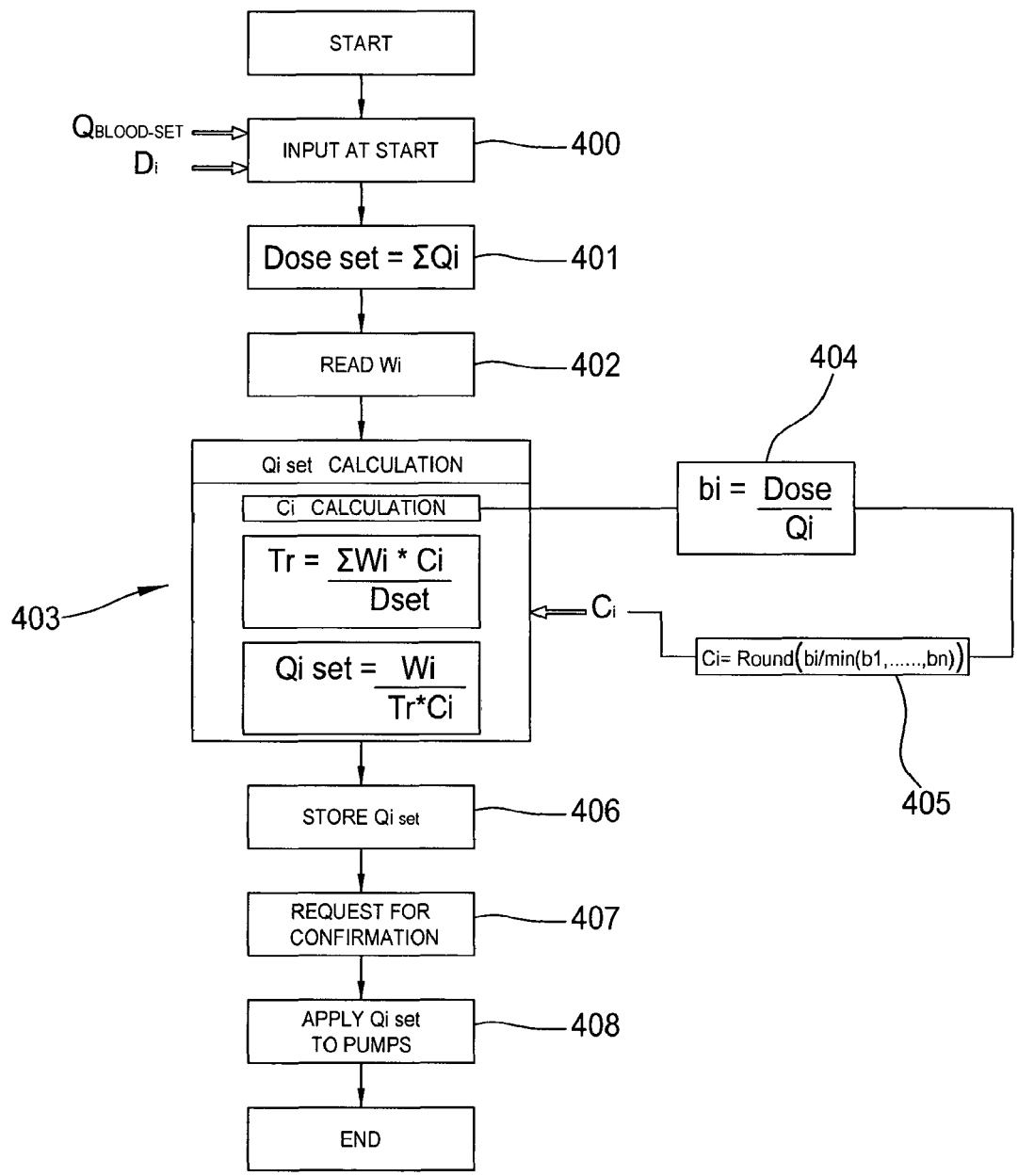
FIG. 9 relates to a flowchart showing calculation of set flow rates in a medical apparatus, e.g. of the type of FIGS. 4-7, according to a further aspect of the invention.

In accordance with a third alternative solution, which is shown in the flowchart of FIG. 9, the control unit 10 may be configured to work in a situation where a number of proposed values $Q_i$ for the flow rates through each one of the lines are available. This may happen before start of the treatment or at a certain moment during the treatment. For instance the proposed $Q_i$ values could be values set by the user (step 400), or values calculated by the control unity to accomplish targets other than synchronization of the emptying of the fluid bags. The set value of the treatment dose $D_{set}$ to be delivered to the patient during the treatment may be either calculated by the control unit based on the flow rates $Q_i$ or set by the user and communicated by to the control unit (step 401). Alternatively, the set value of the dose may be received through an external channel or be pre-stored in a memory connected to the control unit. The blood pump flow rate may be set by the user (step 400) or calculated by the control unit (see below section "Blood pump setting"). The control unit also receives the readings of the scales and thus knows the values $W_i$ of the initial weights of each container (step 402). Note that the volumes $V_i$ of each of the containers may be used as an alternative to the weights also for this third solution. Then, the set value $Q_{iset}$ namely the flow rate to be set in each fluid line may be calculated by the control unit (step 403) dividing a weight ($W_i$) of the respective container by the value of a reference time ($T_r$) multiplied by a respective weighing coefficient ($c_i$) for each respective container using formula:

$$Q_{iset} = (W_i/c_i)/T_r, \text{ where } T_r = (\Sigma W_i \cdot c_i)/\text{Dose}$$

On its turn, $c_i$ for each respective container may be calculated as a function of an intermediary factor $b_i$ obtained (see step 404) by dividing either the dose or the sum of said proposed values $Q_i$ of the flow rates by the respective proposed value $Q_i$. In the example of FIG. 9 each weighing coefficient $c_i$ for each respective container is calculated (step 405) using formula:

$c_i = \text{Round} [b_i/\min(b_1 \ldots b_n)]$, where "$\min(b_1 \ldots b_n)$" is a function selecting the minimum among the $b_i$ factors, and "Round" is a function determining the natural number nearest to the result of quotient $b_i/\min(b_1 \ldots b_n)$.

Once the $Q_{iset}$ values are calculated, they may be stored in a memory (step 406) and then applied to control the pump speeds as described herein below in greater detail with reference to certain embodiments (step 408). In accordance with an optional aspect the control unit may issue a signal to the user interface 12 requesting a confirmation (407) from the user before actually applying the calculated values of $Q_{iset}$ to control the pumps. As a further variant applicable to the above described three alternative solutions, the calculation of the reference time $T_r$ may be done as follows: the control unit may be configured to allow entry of the treatment time T, and calculate the reference time $T_r$ either as the treatment time T or as a sub-multiple of the treatment time T. As disclosed hereinbefore once $T_r$ has been calculated, each flow rate may be set as $Q_{iset} = W_i/T_r$ or as $Q_{iset} = W_i/(T_r \cdot c_i)$ where $c_i$ is an integer from e.g. 1 to 5. In another variant for the calculation of $T_r$, the control unit 10 may be configured to receive one set value set by an operator for one fluid flow rate through one of the lines present in the blood treatment apparatus. For instance, the operator may set the fluid flow rate $Q_{rep1}$ through the pre-dilution infusion fluid line 15, or the fluid flow rate $Q_{rep2}$ through the post-infusion fluid line 25, or the fluid flow rate $Q_{pbp}$ through the pre-blood pump infusion fluid line 21, a fluid flow rate $Q_{dial}$ through the dialysis liquid fluid line 27. The setting may be done through the user interface or via any other input. Once the input of a flow rate to a certain fluid line is set, the control unit is configured to identify the container associated to the fluid line for which the fluid flow rate has been set and to detect the respective initial weight. Then, the control unit may calculate the reference time $T_r$ dividing the initial weight $W_i$ of the identified container by the set value of the fluid flow rate set by the operator. Once $T_r$ has been calculated, each flow rate may be set as $W_i/T_r$ or as $Q_{iset} = W_i/(T_r \cdot c_i)$ where $c_i$ is an integer from e.g. 1 to 5.

In accordance with a fourth alternative solution, the control unit may be configured to execute a synchronization algorithm able to combine the use of proposed values for the set flow rates (for instance initially set by the user or calculated using one or more of the mathematical relations, as above described) with at least a certain degree of synchronization in the emptying of the containers; in other words, a purpose of the algorithm is to minimize the number of user interventions while keeping the flow rates in 'proximity' of some initial settings (which may be manual or computed settings). In practice this algorithm is designed to change according to a certain set percentage the initially set or calculated flow rates in order to reduce as possible the number of container/bag changes across a certain time period, e.g. 24 hours, without substantially changing the initially set or calculated flow rates.

The starting point of the algorithm (see FIG. 12) is the knowledge of:
the full set of proposed flow rates Q (coming either from user settings or from a previous computation step step 500);
the full set of bag/container weight or volume data $W_i$ or $V_i$ providing the initial weight or volume of each container (again either entered by the user or measured with appropriate sensors step 502).

Also the blood flow rate setting for the blood pump may be entered or calculated by the control unit, see step 500. An optional step of calculating a set dose value as sum of the proposed flow rates Q may be present at step 501.

At step 503, an allowed adjustment parameter 'A' is defined as maximum relative change allowed on bag/container change periods in order to optimize bag synchronization and reduce number of user interventions (step 503A). The algorithm also considers 'ratios of interest' $RO_k$ which are parameters defined in the algorithm as ratios between change periods (time between one container change and the next change of the same container) of pairs of containers (step 503B). Ratios of interest are defined for each pair of lines and respective containers. K is an integer which may vary from 1 to M, and M may be pre-stored in the control unit memory or the control unit may be configured to receive it from a user input. The algorithm takes into account that more interventions (container changes) are saved when identifying a '1 to 1' container synchronization ratio between two lines (because in that case the containers of the two lines are changed at the same time), than when having a '1 to 4' ratio. Next table 1 provides the list of the optimum ratios of interest when considering all synchronization ratios up to 'order 5' in relation with a pair of containers indicated as bag1 and bag2. The first 8 $R0_k$ values are used in some examples reported at the end of the detailed description.

TABLE 1 period ratios of interest ranked by 'efficiency'

| k | Bag 1 | Bag 2 | Period ratio Bag1/Bag2 ($R0_k$) | % bag change saved |
|---|---|---|---|---|
| 1 | 1 | 1 | 1.00 | 50% |
| 2 | 1 | 2 | 2.00 | 33% |
| 3 | 1 | 3 | 3.00 | 25% |
| 4 | 1 | 4 | 4.00 | 20% |
| 5 | 2 | 3 | 1.50 | 20% |
| 6 | 1 | 5 | 5.00 | 17% |
| 7 | 3 | 4 | 1.33 | 14% |
| 8 | 2 | 5 | 2.50 | 14% |
| 9 | 3 | 5 | 1.67 | 13% |
| 10 | 4 | 5 | 1.25 | 11% |

In the above table referring for instance to the third more interesting ratio (corresponding to k=3), it is possible to see that k=3 matches with Bag1-Bag2=1 to 3, meaning that Bag2 is changed 3 times while Bag1 is changed once. This corresponds to a change bag period of Bag1 which is 3.0 times longer than the change bag period for Bag2: thus, one user intervention out of 4 is saved compared to a situation where no synchronization at all would be present. Indeed, with k=3 there would be 2 single bag changes of Bag2+1 simultaneous bag changes of Bags 1 and 2 with a total of 3 interventions, whilst in case of no synchronization there would be 3 single bag changes of Bag2+1 single bag change of Bag2, meaning a total of 4 interventions. As K increases the degree of synchronization goes down and, consequently, the number of bag or container changes saved also goes down.

Referring now to the general case of a treatment apparatus with N lines leading to respective N bags or containers, the control unit may be configured to execute the following steps, after the value of A has been selected or predefined (at step 503, see FIG. 13):

Step 504: calculate $T_i$ container change period $T_i=V_i/Q_i$ and rank each circuit according to the calculated container change period, where i=1 to N ($T_i$ increasing with i), Step 505: compute all period ratios $R_{ij}=T_i/T_j$, with i>j Step 506: compare each period ratio $R_{ij}$ to the preset list of ratios of interest $R0_k$, k=1 to M, Step 507: compute the number of degrees of freedom NF; this number if given by the sum of the number of lines less the number of constraints (see further below), Step 508: for each ratio $R_{ij}$ where a k value exists verify that $(1-A) \cdot R0_k < R_{ij} < (1+A) \cdot R0_k$, compute the number of daily saved container changes, Step 509: Select the NF ratios $R_{ij}$ providing the largest number of saved container changes; the selection of the 'best' $R_{ij}$ has to ensure the definition of NF independent relations between NF+1 variables (with the 'NF+1'$^{th}$ relation: $Q_{eff}=\Sigma Q_{fresh\ fluids(i)}+Q_{pfr}$ where $Q_{fresh\ fluids(i)}$ represents any flow rate entering into the bloodlines or the directly into the patient's cardiovascular system, e.g. all infusions, and the dialysis fluid), Step 510: Apply these ratios to compute the optimized flow rates, keeping $Q_{eff}=\Sigma Q_{iset}$ unchanged, and optionally store the calculated $Q_{iset}$, Step 511: optionally request for confirmation by a user of the calculated $Q_{iset}$, Step 512: apply the calculated values $Q_{iset}$ to control each one of the respective pumps.

Concerning the mentioned degrees of freedom NF (step 507 above), the following should be noted. In an apparatus having N lines (e.g. a number of infusion lines, a dialysate line, one or more lines leading to a respective syringe and an effluent line), then the effluent line flow rate may verify condition a fluid balance equation; moreover the syringe line(s) may have a fixed flow rate; the N−2 other lines are infusion or dialysate lines leading to respective containers having fixed volume. In the case where both effluent and syringe bag/container volumes are fixed, the associated bag change periods are also fixed and the N−2 bag change periods for the other lines remain to be defined. As these N−2 periods/flow rates are already linked by the relation $Q_{eff}=\Sigma Q_{fresh\ fluids(i)} \Leftrightarrow Q_{pfr}$, only NF=N−3 relations may be considered for defining all the flow rates. In the scenario where both effluent and syringe bag/container volumes are let free, then the number of degrees of freedom is NF=N−1, since effluent bag volume ($V_{eff}$) and syringe volume ($V_{syr}$) are two additional variables in the system.

In accordance with an aspect, the selection of the NF ratios $R_{ij}$ (step 509 above) providing for the highest number of saved bag changes considers also the 'degrees of freedom' issue. The selection of the 'best' $R_{ij}$ has to ensure the definition of NF independent relations between NF+1 variables (with the 'NF+1'th relation being $Q_{eff}=\Sigma Q_{fresh\ fluids(i)}+Q_{pfr}$.

Note that irrespective of which one of the above described sequences of steps is used for the determination of $Q_{iset}$, once these set values $Q_{iset}$ have been calculated (e.g. using one or more mathematical relations and/or one or more optimization criteria), then the control unit 10 may be configured to display the calculated set values. As mentioned, the control unit may also be configured to ask, or wait, for a confirmation which may be entered by the user, e.g. through action onto the user interface 12. The control unit 10 is designed to control the means for regulating the flow rate based on the calculated set values either automatically (i.e. with no need of any action on the part of an operator), or after the appropriate confirmation is entered and a confirmation signal received at the control unit. In general, and irrespective of which one of the synchronization algorithms above described is used, if the apparatus has one or two syringe lines leading to respective syringe containers S of an anticoagulant solution or a ionic balance solution, the control unit may be configured to calculate the fluid flow rate through said syringe line or lines based on a pre-defined algorithm so that basically there are one or two degree of freedom less and thus 2 flow rates less to calculate left with the algorithm for synchronization of the containers emptying. In such a case the syringe delivery may be controlled based on said predefined algorithm while the emptying of any other container may be fully or partially synchronized with the emptying of the syringe container(s) using one of the synchronization methods above described.

Also in the case where the fourth container leading to said pre-blood pump infusion fluid line 21 includes a regional anticoagulant, for example a citrate based solution, and the second container leading to said post-dilution infusion fluid line 25 includes an ionic balance solution, for example calcium ion based solution 26, the control unit may be configured to calculate the fluid flow rate through said pre-blood pump infusion fluid line 21 and through said post-dilution infusion fluid line 25 based on a pre-defined algorithm. In such a case the delivery through lines 21 and 25 may be controlled based on said a predefined algorithm while the emptying of any other container may be fully or partially synchronized with the emptying of the second and/or fourth container using one of the synchronization methods above described.

EXAMPLE 1

Referring to FIG. 4 the equipment comprises three fresh fluid containers 16, 20, 26. The control unit may be configured to adopt the emptying profiles shown in FIG. 2A, thereby synchronizing the emptying of the three containers. At the beginning of the treatment the scales inform the control unit about the quantity of fluid present in each bag. Then, an overall dose $D_{eff}$ of 5000 ml/h is received by the control unit and a first reference time $T_{r1}$ calculated as sum of the weights of the bags divided by the total dose: (5000+4500+3500) ml/5000 ml/h=2.6 h Each pump flow rate is then calculated as:

$Q_{rep1}$=5000/2.6=1923 ml/h
$Q_{dial}$=4500/2.6=1730 ml/h
$Q_{rep2}$=3500/2.6=1346 ml/h The above flow rates are then set as set values and the respective pumps 18, 21 and 27 controlled accordingly by the control unit 10, as shown in FIG. 2B. After 2.6 hours all bags or containers 16, 20, 26 are simultaneously empty and the control unit is configured to stop the treatment and allow the containers to be substituted with new ones. In FIG. 2A it appears that the new containers have the same weight of 5000 ml and therefore the flow rate of each pump is set at the same flow rate of 5000/$T_{r2}$=1750, as $T_{r2}$ is 3 hours.

EXAMPLE 2

Again referring to FIG. 4, the control unit may alternatively be configured to adopt the emptying profiles shown in FIG. 3A, thereby synchronizing the emptying of two of containers after a first interval and synchronizing the emptying of all three containers after a second interval. At the beginning of the treatment, the scales inform the control unit about the quantity of fluid present in each bag. Then, an overall dose $D_{eff}$ of 3000 ml/h is received by the control unit and a first reference time $T_r$ calculated as sum of the weights of the bags divided by the total dose:

$$T_r=(5000 \cdot c_1+5000 \cdot c_2+5000 \; c_3) \text{ ml}/3000 \text{ ml/h}=4.17 \text{ h}$$

where $c_1$, $c_2$ and $c_3$ are weighing factors in this case respectively set equal to 1, 1 and 2.

Each pump flow rate is then calculated as:
$Q_{rep1}$=5000/(4.17·$c_1$)=1200 ml/h
$Q_{dial}$=5000/(4.17·$c_2$)=1200 ml/h
$Q_{rep2}$=5000/(4.17·$c_3$)=600 ml/h The above flow rates are then imposed as set values and the respective pumps 18, 21 and 27 controlled accordingly by the control unit 10, as shown in FIG. 3B. After 4.17 hours two of the bags/containers 16, 20, 26 are simultaneously empty and the control unit is configured to stop the treatment and allow the two containers to be substituted with new ones. After about other 4.17 hours all three containers are empty and the control unit is configured to stop the treatment and allow the three containers to be substituted with new ones.

EXAMPLE 3

Referring to the circuit of FIG. 4 and to the flowchart of FIG. 9, it may occur that proposed values $Q_i$ for the flow rates through each one of the 3 lines 15, 19 and 25 are available. For instance the proposed $Q_i$ values could be values proposed by the user in order to follow a certain medical prescription, or they could be values calculated by the control unity to accomplish targets other than synchronization of the emptying of the fluid bags. In this example the following proposed Q values are given:

$Q_1$=1900 ml/h—proposed flow rate for $Q_{DIAL}$ through line 19
$Q_2$=650 ml/h—proposed flow rate for $Q_{REP1}$ through line 15
$Q_3$=450 ml/h—proposed flow rate for $Q_{REP2}$ through line 25

Figure 10:
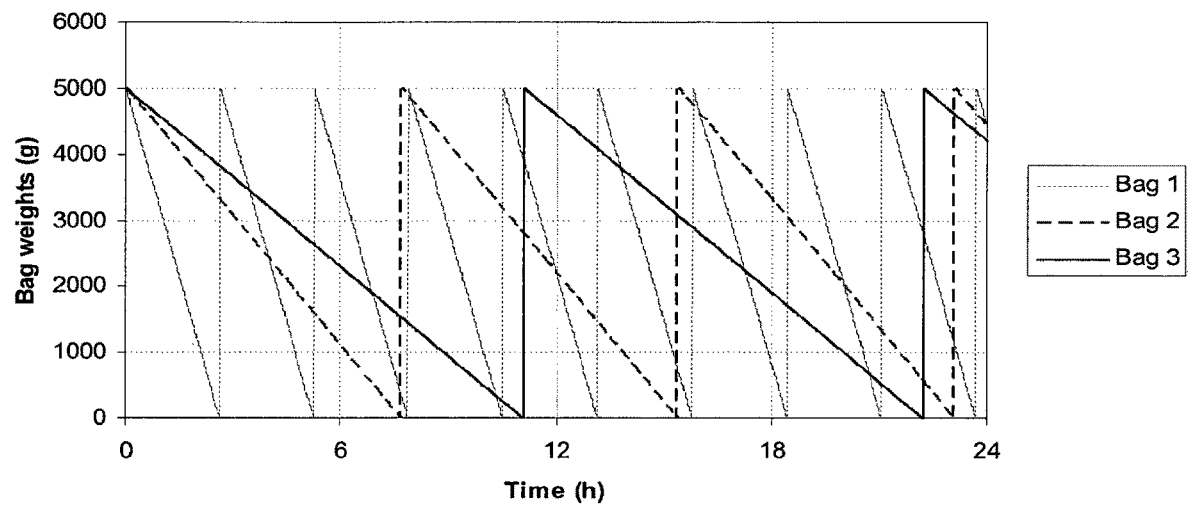
FIG. 10 shows a chart, relative to the emptying profiles of three bags/containers in a case where certain flow rates have been imposed for each one of the lines leading to the three bags/containers; the vertical axis in FIG. 10 represents the weight of each one of three bags/containers and the horizontal axis represents the emptying time.

Each container 20, 16 and 26 is a 5 L bag, and the set dose is the sum of the above Q values, namely 3000 ml/h In the case where no synchronization is implemented, then the situation would be as per FIG. 10, where 14 interventions for bag changes are required every 24 hours.

In case of bag emptying synchronization where the machine attempts to achieve a certain degree of synchronisation without substantially changing the proposed flow rates, $c_1$, $c_2$ and $c_3$ are calculated as follows:

First, the control unit calculates intermediary parameters $B_i$ using the formula:

$$b_i=\text{Dose}/Q_i \text{ (where is the flow rate of the } i^{th} \text{ pump)}$$

The following results are obtained:
$b_1$=3000/1900=1.58
$b_2$=3000/650=4.62
$b_3$=3000/450=6.67

The value of $c_i$ are obtained by normalizing the values of $b_i$ with respect to their minimum and rounding the result to the closest natural number, using the formula:

$$c_i=\text{Round}(b_i/\min(b_1 \ldots b_n))$$

With the following results:
$c_1$=Round(1.58/1.58)=1
$c_2$=Round(4.62/1.58)=3
$c_3$=Round(6.67/1.58)=4

Figure 11:
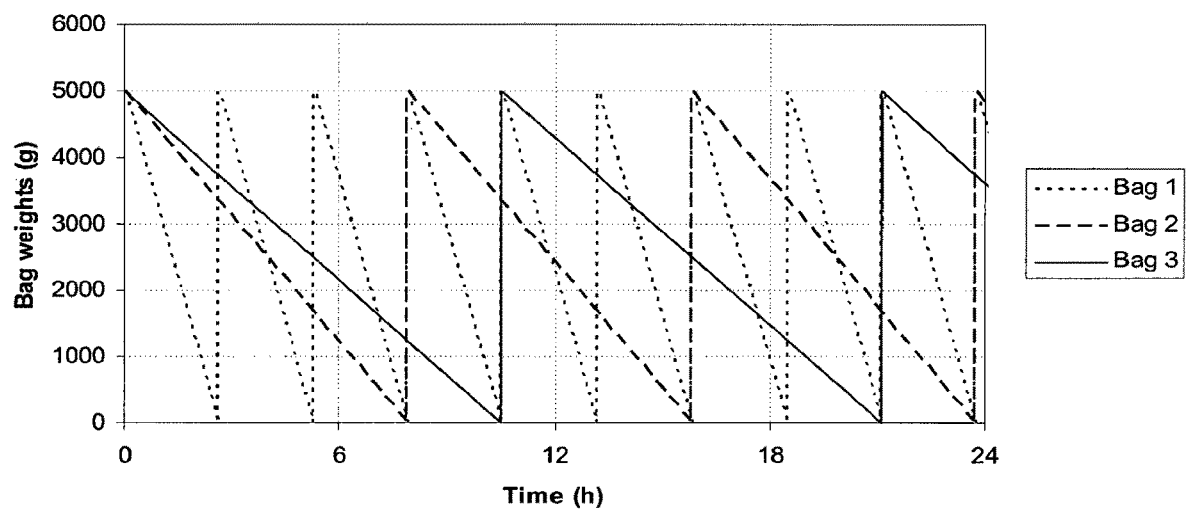
FIG. 11 shows a chart, relative to the emptying profiles of three bags/containers in accordance with the flowchart of FIG. 9, where the vertical axis represents the weight of each one of three bags/containers and the horizontal axis represents the emptying time.

From $c_1$, $c_2$ and $c_3$ the flow rate $Q_i$ of a given pump is calculated as follows:

$$T_r=(\Sigma W_i/c_i)/\text{Dose}$$

$$Qi=(W_i/c_i)/T_r$$

where $W_i$ is the initial weight of the Bag
$T_r$=(5000/1+5000/3+5000/4)/3000=2.6389 h
$Q_{1set}$=(5000/1)/2.6389=1895 ml/h
$Q_{2set}$=(5000/3)/2.6389=632 ml/h
$Q_{3set}$=(5000/4)/2.6389=474 ml/h As shown in FIG. 11, the number of interventions for bag changes during 24 hours goes down to 9, while keeping the flow rates quite close to the initially proposed flow rates.

EXAMPLE 4

Figure 12:
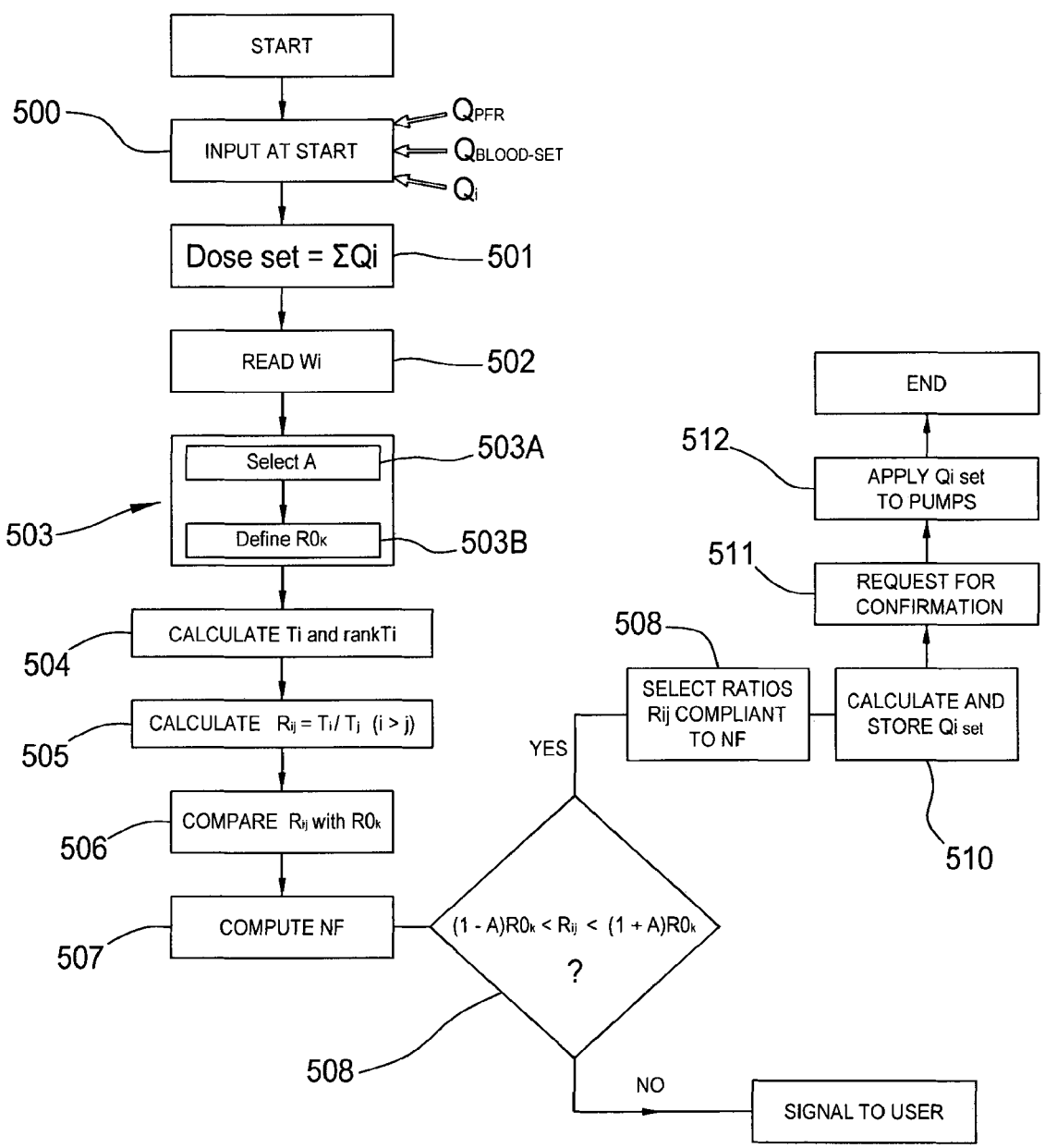
FIG. 12 is a flowchart showing calculation of set flow rates in a medical apparatus, e.g. of the type of FIGS. 4-7, according to another aspect of the invention.

The following is a general example according to the fourth synchronization solution described above which follows the exemplifying flowchart of FIG. 12.

$Q_{BLOOD}$ and the proposed $Q_i$ values are set by the user or calculated by the control unit at step 500. At this step, the patient fluid removal rate $Q_{PFR}$ is fixed or entered by the user at 100 ml/h. Then the dose value is set or calculated (step 501) and the volume of the of each bag detected or entered by the user (step 502).

The following parameters are selected or preprogrammed (step 503):

number ratios of interest 1 to 8 (M=8), allowed flow rate adjustment of 10% (A=0.10) on the initially proposed $Q_i$.

It is assumed that the apparatus comprises a circuit similar to that of FIG. 2 with a syringe pump connected to the blood return line instead of infusion line 25. Effluent and Syringe bag/container volumes are fixed. At step 504 the $T_i$ values are calculated and ranked by the control unit.

Table 2 below recaps the initial flow rates $Q_i$ ($2^{nd}$ column), the bag volumes ($3^{rd}$ column), the change bag periods $T_i$ ($4^{th}$ column) using the initial Q values and the corresponding number of daily bag changes ($5^{th}$ column).

TABLE 2

| circuit | flow rate (initial) (ml/h) | bag volume (ml) | change bag period (h) | nb of daily bag changes (day$^{-1}$) |
|---|---|---|---|---|
| PBP | 1000 | 5000 | 5.00 | 4.80 |
| Dial | 1200 | 5000 | 4.17 | 5.76 |
| Rep | 350 | 3000 | 8.57 | 2.80 |
| syringe | 15 | 50 | 3.33 | 7.20 |
| PFR | 100 | — | — | — |
| Effluent | 2665 | 5000 | 1.88 | 12.79 |
| Total | | | | 33.35 |

Table 3 below ranks the change bag periods Ti from the shortest to the longest.

TABLE 3

| | Shortest period | | | | Longest period |
|---|---|---|---|---|---|
| Circuit index 'i' | 1 | 2 | 3 | 4 | 5 |
| Circuit ID | Effluent | syringe | Dial | PBP | Rep |
| Period (h) | 1.88 | 3.33 | 4.17 | 5.00 | 8.57 |
| nb daily bag changes (day$^{-1}$) | 12.79 | 7.20 | 5.76 | 4.80 | 2.80 |

At step 505, the $R_{ij}=T_i/T_j$ (i>j) are calculated by the control unit. Table 4 provides the computation of period ratios $$R_{ij}=T_i/T_j (i>j)$$

TABLE 4

| | j | | | | |
|---|---|---|---|---|---|
| i | 1 | 2 | 3 | 4 | 5 |
| 1 | | | | | |
| 2 | 1.78 | | | | |
| 3 | 2.22 | 1.25 | | | |
| 4 | 2.67 | 1.50 | 1.20 | | |
| 5 | 4.57 | 2.57 | 2.06 | 1.71 | |

Then at step 506, the control unit compares the $R_{ij}$ ratios to the ratios of interests $R0_k$ of table 1 creating the ratios $R_{ij}/R0_k$. Table 5 shows the ratios $R_{ij}/R0_k$; At step 508 the control unit table 5 also checks the ratios $R_{ij}/R0_k$ which stay within the 'A' criterion, namely those which verify the condition:

$$(1-A)R0_k < R_{ij} < (1+A)R0_k.$$

Note that table 5 also includes an identification of ratios which result within 'A' criterion (see cells with underlined values, namely those which verify the condition:

$$(1-A)R0_k < R_{ij} < (1+A)R0_k).$$

TABLE 5

| R0k | $R_{21}$ | $R_{31}$ | $R_{41}$ | $R_{51}$ | $R_{32}$ | $R_{42}$ | $R_{52}$ | $R_{43}$ | $R_{53}$ | $R_{54}$ |
|---|---|---|---|---|---|---|---|---|---|---|
| $R0_1$ | 1.78 | 2.22 | 2.67 | 4.57 | 1.25 | 1.50 | 2.57 | 1.20 | 2.06 | 1.71 |
| $R0_2$ | 0.89 | 1.11 | 1.33 | 2.28 | 0.63 | 0.75 | 1.29 | 0.60 | <u>1.03</u> | 0.86 |
| $R0_3$ | 0.59 | 0.74 | 0.89 | 1.52 | 0.42 | 0.50 | 0.86 | 0.40 | 0.69 | 0.57 |
| $R0_4$ | 0.44 | 0.56 | 0.67 | 1.14 | 0.31 | 0.38 | 0.64 | 0.30 | 0.51 | 0.43 |
| $R0_5$ | 1.18 | 1.48 | 1.78 | 3.05 | 0.83 | <u>1.00</u> | 1.71 | 0.80 | 1.37 | 1.14 |
| $R0_6$ | 0.36 | 0.44 | 0.53 | <u>0.91</u> | 0.25 | 0.30 | 0.51 | 0.24 | 0.41 | 0.34 |
| $R0_7$ | 1.33 | 1.67 | 2.00 | 3.43 | <u>0.94</u> | 1.13 | 1.93 | <u>0.90</u> | 1.54 | 1.29 |
| $R0_8$ | 0.71 | 0.89 | <u>1.07</u> | 1.83 | 0.50 | 0.60 | <u>1.03</u> | 0.48 | 0.82 | 0.69 |

At step 507 (this step may be executed at any time before step 509 below described), the control unit computes the degrees of freedom NF. Table 6 indicates the number of degrees of freedom (NF).

TABLE 6

| circuit | Flow rate | Bag volume | Degrees of freedom | NF |
|---|---|---|---|---|
| PBP | adjustable | fixed | Yes | NF = 3 − 1 = 2 |
| Dial | adjustable | fixed | Yes | |
| Rep | adjustable | fixed | Yes | |
| syringe | fixed | fixed | No | |
| Effluent | fixed | fixed | No | |

Then the control unit provides a computation of the number of bag change saved for all $R_{ij}$ within the above criterion for the A parameter and identifies the most effective combinations complying also with the available NF=2 degrees of freedom.

Table 7 shows this computation of the number of bag change saved and identifies (see arrow) of the NF=2 most effective combinations.

Table 7

|  | i/j | Bag 1 | Bag 2 | nb daily bag changes | nb saved bag changes |
|---|---|---|---|---|---|
| Best =>> | 5/3 | 1 | 2 | 8.6 | 2.9 |
|  | 4/2 | 2 | 3 | 12.0 | 2.4 |
| Best =>> | 5/1 | 1 | 5 | 15.6 | 2.6 |
|  | 3/2 | 3 | 4 | 13.0 | 1.9 |
|  | 4/3 | 3 | 4 | 10.6 | 1.5 |
|  | 4/1 | 2 | 5 | 17.6 | 2.5 |
|  | 5/2 | 2 | 5 | 10.0 | 1.4 |

Then the control unit calculates and optionally stores the flow rates.

Table 8 provides a summary of selected $R_{ij}$ ratios and flow rate relations obtained using below Equations:

$$T_i = \frac{V_i}{Q_i}$$

$$R_{ij} = \frac{T_i}{T_j}$$

Thus:

$$Q_i = V_i/T_i = V_i/(R_{ij} \cdot T_j) = V_i/(R_{ij} \cdot V_j/Q_j)$$

Using the flow rate relations derived from selected $R_{ij}$ and related $R0_k$ values, the above equation leads to the adjusted value for $Q_i$, namely:

$$Q_i = \frac{V_i}{V_j} \times \frac{Q_j}{R0_k}$$

TABLE 8

| $R_{ij}$ ID | Target $R0_k$ | $R0_k$ value | Flow rate relation* |
|---|---|---|---|
| $R_{53}$ | $R0_2$ | 2.00 | Q5 = 0.30 × Q3 |
| $R_{51}$ | $R0_6$ | 5.00 | Q5 = 0.12 × Q1 |

Then follows the computation of flow rates using $R0_k$ ratios selected in table 8. The adjusted flow rates are recapped in Table 9 below which clarifies how with a relatively small adjustment to the initially proposed flow rates a certain degree of synchronization in the container emptying has been achieved thus saving significant time in container changes.

TABLE 9

| circuit | flow rate (initial) (ml/h) | Adjusted flow rate (computed) | nb of daily bag changes day$^{-1}$ | Number of saved user interventions per day |
|---|---|---|---|---|
| PBP | 1000 | 1164 | 5.59 |  |
| Dial | 1200 | 1066 | 5.12 | 2.56 |
| Rep | 350 | 320 | 2.56 | 2.56 |
| syringe | 15 | 15 | 7.20 |  |
| PFR | 100 | 100 | — |  |
| Effluent | 2665 | 2665 | 12.79 |  |
| Total |  |  | 33.26 | 5.12 |
| Daily number of user interventions |  |  | 28.1 |  |

EXAMPLE 5

Reference is made to an apparatus as shown in FIG. 4, provided with 4 fluid pumps (Dialysate pump 21, Replacement pump 27, Replacement pump 15, Effluent pump 17) and thus capable of running a HDF therapy.
Prescription:
Patient: BW=65 kg
blood flow rate: $Q_{BLOOD}$=220 ml/min
patient fluid removal rate: $Q_{pfr}$=100 ml/h
CRRT dose $D_{eff\text{-}set}$=38 ml/kg/h, where the is defined as 'Urea dose'
The following criteria are stored in memory 10a:
dialysate flow rate ($Q_{dial}$): 0 to 6000 ml/h
PRE-replacement flow rate ($Q_{rep1}$): 0 to 4000 ml/h
POST-replacement flow rate ($Q_{rep2}$): 0200 to 4000 ml/h
no specific hemofilter/dialyzer related data
The operator selects:
blood predilution ratio: $R_2$>0.10
minimize fluid consumption
The control unit 10 then computes the flow rates as follows:

$$Q_{eff} = Q_{dial} + Q_{rep1} + Q_{rep2} + Q_{pfr} \text{ to be minimized} \quad \text{Eq.1:}$$

$$D_{set\text{-}urea} = Q_{BLOOD}/(Q_{BLOOD}+Q_{rep1}) \times Q_{eff} = 65 \times 38 = 2470 \text{ ml/h} \quad \text{Eq.2:}$$

$$Q_{rep2} > 200 \text{ ml/min} \quad \text{Eq.3:}$$

$$R_2 > 0.10 \quad \text{Eq.4:}$$

In order to meet the Urea dose target while minimizing fluid consumption ($Q_{eff}$), it is necessary to maximize the ratio $Q_{BLOOD}/(Q_{BLOOD}+Q_{rep1})$ According to the set constraints, this requires to set $Q_{rep1}$=0.10×$Q_{BLOOD}$=1320 ml/h (from eq.4).
Equation 2 allows to define $Q_{eff}$=2470×(1+0.10/1)=2717 ml/h.
$Q_{dial}$ and $Q_{rep2}$ have then to be defined from:

$$Q_{dial} + Q_{rep2} = 2717 - 100 - 1320 = 1297 \text{ ml/h} \quad \text{Eq.1bis:}$$

$$Q_{rep2} > 200 \text{ ml/h} \quad \text{Eq.3:}$$

From the above first phase of computation, the following has been defined:
$Q_{eff}$=2717 ml/h,
$Q_{rep1}$=1320 ml/h,
a relation between Qdial and $Q_{rep2}$ (Qdial+$Q_{rep2}$=1297 ml/h, directly derived from Qeff=ΣQi),
a condition on $Q_{rep2}$ (>200 ml/h).
In other words some flow rates are not completely defined. As above discussed in connection with the fourth solution of synchronization, a synchronization algorithm may be performed by the control unit from an arbitrary set of values; for example the above calculated flow rates where Qdial=550 ml/h (⇒Qrep2=747 ml/h). The issue in this case is the choice of the 'allowed adjustment' parameter A, since a specific flow rate range is defined for Qdial [0;1297], allowing for a large range of bag change period. For this application case, the value of 'A' is selected at 0.3 (while 0.1 was used in example 6).

$Q_{rep1}$, as well as $V_{eff}$, are fixed; then number of degrees of freedom is NF=4−3=1 and consequently one single synchronization relation may be introduced. The initial input data to the synchronization algorithm are indicated in Table 10 while in Table 11 a ranking of change bag periods Ti is given.

TABLE 10

| circuit | flow rate (initial) (ml/h) | bag volume (ml) | change bag period (h) | nb of daily bag changes (day$^{-1}$) |
|---|---|---|---|---|
| Pre | 1320 | 5000 | 3.79 | 6.34 |
| Dial | 550 | 5000 | 9.09 | 2.64 |
| Post | 747 | 5000 | 6.69 | 3.59 |
| PFR | 100 | — | — | — |
| Effluent | 2717 | 5000 | 1.84 | 13.04 |
| Total | | | | 25.60 |

TABLE 11

| Circuit index 'i' | Shortest period 1 | 2 | 3 | Longest period 4 |
|---|---|---|---|---|
| Circuit ID | Effluent | Qpre | Qpost | Qdial |
| Period (h) | 1.84 | 3.79 | 6.69 | 9.09 |
| nb daily bag changes (day$^{-1}$) | 13.04 | 6.34 | 3.59 | 2.64 |

Then the control unit makes a computation of period ratios $R_{ij}=T_i/T_j$ (i>j). Table 12 recaps the computed values for $$R_{ij}=T_i/T_j.$$

TABLE 12

| | | | j | | |
|---|---|---|---|---|---|
| i | 1 | 2 | 3 | 4 | 5 |
| 1 | | | | | |
| 2 | 2.06 | | | | |
| 3 | 3.64 | 1.77 | | | |
| 4 | 4.94 | 0.70 | 1.36 | | |

Then the control unit compares the $R_{ij}$ ratios to the ratios of interests $R0_k$ of table 1 creating the ratios $R_{ij}/R0_k$ and also checks the ratios $R_{ij}/R0_k$ which stay within the 'A' criterion, namely those which verify the condition:

$$(1-A)\cdot R0_k < R_{ij} < (1+A)\cdot R0_k.$$

Below table 13 an identification of ratios which result within 'A' criterion (see cells with underlined values, namely those which verify the condition:

$$(1-A)R0_k < R_{ij} < (1+A)\cdot R0_k).$$

TABLE 13

| R0k | $R_{21}$* | $R_{31}$** | $R_{41}$** | $R_{32}$** | $R_{42}$** | $R_{43}$*** |
|---|---|---|---|---|---|---|
| R0$_1$ | 2.06 | 3.64 | 4.94 | 1.77 | <u>0.70</u> | <u>1.36</u> |
| R0$_2$ | 1.03 | 1.82 | 2.47 | <u>0.88</u> | 0.35 | <u>0.68</u> |
| R0$_3$ | 0.69 | <u>1.21</u> | 1.65 | 0.59 | 0.23 | 0.45 |
| R0$_4$ | 0.51 | <u>0.91</u> | <u>1.24</u> | 0.44 | 0.17 | 0.34 |
| R0$_5$ | 1.37 | 2.42 | 3.29 | <u>1.18</u> | 0.46 | <u>0.91</u> |
| R0$_6$ | 0.41 | <u>0.73</u> | <u>0.99</u> | 0.35 | 0.14 | 0.27 |
| R0$_7$ | 1.54 | 2.73 | 3.71 | 1.33 | 0.52 | <u>1.02</u> |
| R0$_8$ | 0.82 | 1.45 | 1.98 | <u>0.71</u> | 0.28 | <u>0.54</u> |

*not considered as $Q_{eff}$ and $Q_{rep1}$ assumed already fixed
**selection with adjustment coefficient of 0.3 (ratio depending on $Q_{dial}$ or $Q_{rep2}$)
**selection with adjustment coefficient of 0.5 (ratio depending on $Q_{dial}$ and $Q_{rep2}$)

The number of degrees of freedom NF are then identified. Table 14 indicates the number of degrees of freedom (NF).

TABLE 14

| circuit | Flow rate | Bag volume | Degrees of freedom | NF |
|---|---|---|---|---|
| Pre | fixed | fixed | No | NF = 2 − 1 = 1 |
| Dial | adjustable | fixed | Yes | |
| Post | adjustable | fixed | Yes | |
| Effluent | fixed | fixed | No | |

Then the control unit identifies the best relation with NF=1 and respecting the limitations on the A value as well as the fixed parameters. Tables 15 and 16 indicate that the 'best' relation to introduce is $Q_{rep2}=Q_{eff}/3$, allowing to save more than 4 user interventions a day (~17%). Note that relation 2/1 (Qrep1−$Q_{eff}$) is discarded since both $Q_{eff}$ and $Q_{rep1}$ are fixed. Relation 4/2 ($Q_{dial}$−$Q_{rep1}$) leads to $Q_{dial}=Q_{pre}$ which is not compatible with $Q_{eff}=\Sigma Q_i$.

Table 15

| | i/j | Bag 1 | Bag 2 | nb daily bag changes | nb saved bag changes |
|---|---|---|---|---|---|
| | 4/2 | 1 | 1 | 9.0 | 4.49 |
| | 4/3 | 1 | 1 | 6.2 | 3.11 |
| | 2/1 | 1 | 2 | 19.4 | 6.46 |
| | 3/2 | 1 | 2 | 9.9 | 3.31 |
| | 4/3 | 1 | 2 | 6.2 | 2.08 |
| Best => | 3/1 | 1 | 3 | 16.6 | 4.16 |
| | 3/1 | 1 | 4 | 16.6 | 3.33 |
| | 4/1 | 1 | 4 | 15.68 | 3.14 |
| | 3/2 | 2 | 3 | 9.92 | 1.98 |
| | 4/3 | 2 | 3 | 6.23 | 1.25 |

TABLE 16

| $R_{ij}$ ID | Target $R0_k$ | $R0_k$ value | Flow rate relation* |
|---|---|---|---|
| $R_{31}$ | $R0_3$ | 3.00 | Q3 = 0.333 × Q1 |

The above selected $R_{ij}$ ratios and flow rate relations (table 16) are used by the control unit for computation of flow rates $Q_{iset}$ (in this case $Q_3$ and $Q_1$ respectively corresponding to $Q_{rep2}$=391.3 ml/h and $Q_{dial}$=905.7 ml/h) as per below table 17.

TABLE 17

| circuit | flow rate (initial) (ml/h) | Adjusted flow rate (computed) | nb of daily bag changes day$^{-1}$ | Number of saved user interventions per day |
|---|---|---|---|---|
| Pre | 1320 | 1320 | 6.34 | |
| Dial | 550 | 905.7 | 4.35 | 4.35 |
| Post | 747 | 391.3 | 1.88 | |
| PFR | 100 | 100 | — | |
| Effluent | 2717 | 2717 | 13.04 | |
| Total | | | 25.60 | 4.35 |
| Daily number of user interventions | | | 21.3 | |

To secure the result, the algorithm might be repeated using a different set of initial flow rates; in this case it is verified that the same result is obtained with $Q_{dial}$=100 ml/h ($\Rightarrow Q_{rep2}$=1197) as initial flow rate (same result except permutation of $Q_{rep2}$ and $Q_{dial}$ values).

Note that in the above example, in the case adjustment of Qrep1 is allowed, then NF=2 and 6.5 additional user interventions may be saved by setting $Q_{rep1}$=$Q_{eff}$/2 (computation steps not reported).

Initial Setting

As above explained the operator may select a prescribed dose value. The prescribed dose value may also be calculated at the beginning of the treatment by the control unit or it may be pre-stored in a memory connected with the control unit. Based on the prescribed dose value and on the value of the weighing coefficients $c_i$, the control unit may determine the set flow rates on each line in order to achieve the desired level of emptying/filling synchronization. Alternatively to the dose setting the control unit may receive a set flow rate for one of the fluid lines 15, 19, 22, 25 and the value of the weighing coefficients $c_i$, and then determine the set flow rates on each line in order to achieve the desired level of emptying/filling synchronization.

In a further alternative a treatment time T may be entered which is then used to calculate $T_r$ and then the flow rates in each line based on $T_r$ and $c_i$.

The control unit may also allow entry by an operator of the set value for a blood flow $Q_{BLOOD}$ through the blood withdrawal or blood return line, and/or it may be configured to calculate the set value for the blood flow to be set (see below section "Blood pump setting").

Finally the control unit is configured to allow entry of the fluid removal rate ($Q_{pfr}$) from the patient, or of the treatment time (T) and of the weight loss (WL) to be imposed over said treatment time (T).

In other words, by specifying the set values for dose (or for the flow rate through one of the fluid lines or for the treatment time T), fluid removal rate (or the weight loss+treatment time), and the blood flow rate (unless it is automatically calculated), the apparatus may be very easily initialized and treatment may start with the emptying of the containers or bags duly synchronized.

In the present description it has been explained that the control unit is configured to receiving weight signal corresponding to the weight $W_i$ as measured by a corresponding scale associated to each container: the weight of each respective container $W_i$ used for the calculation of the set values of the fluid flow rates is usually determined at the beginning of the treatment or subsequent to each bag-substitution before restarting the treatment; however, each weight may also be determined at prefixed checkpoints during treatment or responsive to a user input, such that the control unit may be designed to be able to synchronize the emptying of the bags at any time.

Blood Pump Setting

In the above description it has been indicated that the blood pump may be controlled by the control unit 10 using a set value of the blood flow rate $Q_{BLOOD}$ entered by the user. More in general, the control unit 10 may allow entry by an operator of the set value for a blood flow $Q_{BLOOD}$ through the blood withdrawal or blood return line, or it may be configured to calculate the set value for the blood flow to be set. In this latter case the calculated value for the set blood flow could be calculated based on the value of the flow rate determined in one of the fluid lines: for instance the blood flow rate could be calculated to be proportional to calculated value of the flow rate through pre-blood pump infusion line (or viceversa the pre-blood pump infusion line flow rate could be calculated to be proportional to $Q_{BLOOD}$) Alternatively, the blood flow rate may be calculated based on a sensed value of a patient parameter or of a treatment parameter, e.g. by way of non-limiting examples: the pressure sensed by pressure sensor 6b in tract 6a of the blood withdrawal line, a measured blood recirculation fraction re-circulating from the blood return line 7 into the blood withdrawal line 6, a measured value of hemo-concentration measured in correspondence of one of the blood lines 6, 7, a measured value of transmembrane TMP pressure across the filter semipermeable membrane 5.

In any case, the control unit 10 may control the blood pump using either the entered or the calculated set value for the blood flow $Q_{BLOOD}$.

Safety Features

It should be noted that the control unit may be designed to include some safety features: indeed it the filtration fraction is an important factor to be considered. Since the flow rates may be automatically set by the control unit 10, it is possible to ensure that all pumps infusing in post-dilution will not cause an excessive filtration fraction (e.g. post-dilution flow rate >20% of blood flow rate). In this respect the control unit 10 may be configured to check if the calculated set value for the fluid flow rate through the post-dilution infusion line is higher than a prefixed fraction of the blood flow rate and in the affirmative activate a correction procedure. The correction procedure may comprise issuing a warning to the user interface, or it may comprise issuing a command to stop the treatment, or it may comprise correcting the delivery of fluid through one or more of the other lines, or (in case for instance the blood treatment apparatus includes a switch on the post-dilution line) issuing a command to switch 100 and/or 101 to temporary connecting a post-dilution fluid line to the blood withdrawal line. For instance referring to FIG. 7, the control unit could switch one or more pumps infusing in post-dilution to pre-dilution or dialysate mode. The switch could be accompanied by majoring the flow rate of the pump(s) that have been switched and reducing the other pump flow rates. This condition is maintained until the weight of the bag(s) that was switched decreases to a level making it possible to infuse in post-dilution without exceeding the maximum allowed filtration fraction. Alternatively, it is possible to have the control unit 10 configured to maintain the post-dilution pump as such but rather decrease its flow rate such that the emptying time is differed by adjusting its weighting factor.

Composition of the Fluid Containers

All containers of fresh fluid may comprise a fluid (e.g. a replacement solution) having a same composition. The fact that the flow rates are not set individually implies that if the same type of composition is used during the treatment for containers there is no unexpected outcome regarding the electrolytic balance and/or acid-base equilibrium of the patient.

It may be envisaged that a container of fresh fluid comprises a fluid having a composition different from that of the other containers of fresh fluid: for instance the fourth container may contain an anticoagulant, such as a citrate solution; in this case the control unit 10 is configured to calculate the set value of fluid flow rate through the pre-blood pump infusion line to be proportional to the set or calculated value of the blood pump flow rate for achieving an adequate anticoagulation level. The other pump flow rates are adjusted so as to become empty at the same time as the citrate bag. Alternatively, the control unit could use the citrate bag in a way that it is not synchronized with the emptying of the other fluid bags and is thus managed separately (e.g. flow rate is proportional to blood flow rate). In a further alternative, fourth bag emptying is synchronized with the other bags and the blood pump flow rate setting is adjusted so as to be proportional to the citrate pump flow rate. Of course one could also envisage that all infusion bags used be citrate-containing bags: in this case synchronization may be made with no problems. Notice that in case the fourth bag includes a regional anticoagulant, e.g. a citrate based solution, then one post-dilution line including a calcium ion based solution may be present: for instance referring to FIG. 2 container 23 may include a citrate based solution and container 26 a calcium ion solution. Of course, one or both lines 22 and 27 may be associated with a bag container and cooperate with a peristaltic pump (as shown in FIG. 2) or may include a syringe delivery system.

One of the advantages of the claimed solution as well as of the above described embodiments is logistic since the frequency of bag/container changes is reduced.

One other advantage is a positive impact on the treatment since lesser interruptions help in providing more continuous and accurate treatment.

One further positive aspect which may be provided by certain aspects of the present invention is a simplification in setting of treatment prescription.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

Here below the components and corresponding reference numerals used in the detailed description are listed.

| Part | Reference numeral |
|---|---|
| extracorporeal blood treatment apparatus | 1 |
| filtration unit | 2 |
| primary chamber | 3 |
| secondary chamber | 4 |
| semi-permeable membrane | 5 |
| blood withdrawal line | 6 |
| tract | 6a |
| blood return line | 7 |
| bubble trap | 8 |
| bubble sensor | 8a |
| Clamp | 9 |
| control unit | 10 |
| blood pump | 11 |
| user interface | 12 |
| an effluent fluid line | 13 |
| an effluent fluid container | 14 |
| pre-dilution fluid line | 15 |
| infusion fluid containers | 16, 23, 26 |
| dialysis fluid line | 19 |
| dialysis fluid container | 20 |
| dialysis pump | 21 |
| a post-dilution fluid line | 25 |
| effluent fluid pump | 17 |
| infusion pumps | 18, 27 |
| pre-blood pump infusion line | 22 |
| line switches | 100, 101 |

The invention claimed is:

1. An apparatus for extracorporeal treatment of fluid comprising:

a filtration unit having a primary chamber and a secondary chamber separated by a semi-permeable membrane;

a blood withdrawal line connected to an inlet of the primary chamber and a blood return line connected to an outlet of the primary chamber, the blood withdrawal line and the blood return line configured to connect to a patient cardiovascular system;

a blood pump configured to control the flow of blood through the blood withdrawal line and the blood return line;

an effluent fluid line connected, at one end thereof, to an outlet of the secondary chamber and at its other end to a waste container;

at least two fluid lines selected from the group of fluid lines comprising:

a pre-dilution infusion fluid line connected at one end thereof to the blood withdrawal line and at its other end to a first container of fresh fluid, a post-dilution infusion fluid line connected at one end thereof to the blood return line and at its other end to a second container of fresh fluid, a dialysis liquid fluid line connected at one end thereof to an inlet of the secondary chamber and at its other end to a third container of fresh fluid, and a pre-blood pump infusion fluid line connected at one end thereof to a fourth container of fresh fluid and at its other end to the blood withdrawal line in a region of the blood withdrawal line which is positioned in use upstream the blood pump;

a control unit connected to and configured to operate the blood pump;

the control unit connected to and configured to operate a means for regulating flow of effluent fluid through the effluent fluid line to deliver effluent fluid to the waste container at an effluent fluid flow rate ($Q_{eff}$)

the control unit connected to and configured to operate a means for regulating flow of pre-dilution infusion fluid through the pre-dilution infusion fluid line at a pre-dilution infusion fluid flow rate ($Q_{rep1}$) when the at least two fluid lines comprise the pre-dilution fluid line;

the control unit connected to and configured to operate a means for regulating flow of post-dilution infusion fluid through the post-dilution infusion fluid line at a post-dilution infusion fluid flow rate ($Q_{rep2}$) when the at least two fluid lines comprise the post-dilution infusion fluid line;

the control unit connected to and configured to operate a means for regulating flow of dialysis liquid through the dialysis liquid fluid line at a dialysis liquid fluid flow rate $Q_{dial}$ when the at least two fluid lines comprise the dialysis liquid fluid line;

the control unit connected to and configured to operate a means for regulating flow of pre-blood pump infusion fluid through the pre-blood pump infusion fluid line at a pre-blood pump infusion fluid flow rate ($Q_{pbp}$) when the at least two fluid lines comprise the pre-blood pump infusion fluid line;

and wherein the control unit is further configured to calculate set values ($Q_{iset}$) of the fluid flow rates of the at least two fluid lines such that:

an emptying time of each container of fresh fluid connected at the other end of the at least two fluid lines and a filling time of the waste container are multiples of a same reference time ($T_r$); and a sum of the set values ($Q_{iset}$) of the fluid flow rates through the at least two fluid lines and of a patient fluid removal rate ($Q_{pfr}$) is equal to the effluent fluid flow rate ($Q_{eff}$);

wherein, when the at least two fluid lines comprise the pre-dilution infusion fluid line, one set value ($Q_{iset}$) comprises the pre-dilution infusion fluid flow rate ($Q_{rep1}$) and the control unit is configured to operate the means for regulating flow of the pre-dilution infusion fluid through the pre-dilution infusion fluid line such that an emptying time of the first container of fresh fluid and the filling time of the waste container are multiples of the same reference time ($T_r$);

wherein, when the at least two fluid lines comprise the post-dilution infusion fluid line, one set value ($Q_{iset}$) comprises the post-dilution infusion fluid flow rate ($Q_{rep2}$) and the control unit is configured to operate the means for regulating flow of the post-dilution infusion fluid through the post-dilution infusion fluid line such that an emptying time of the second container of fresh fluid and the filling time of the waste container are multiples of the same reference time ($T_r$);

wherein, when the at least two fluid lines comprise the dialysis liquid infusion fluid line, one set value ($Q_{iset}$) comprises the dialysis liquid fluid flow rate ($Q_{dial}$) and the control unit is configured to operate the means for regulating flow of the dialysis liquid through the dialysis liquid fluid line such that an emptying time of the third container of fresh fluid and the filling time of the waste container are multiples of the same reference time ($T_r$); and wherein, when the at least two fluid lines comprise the pre-blood pump infusion fluid line, one set value ($Q_{iset}$) comprises the pre-blood pump infusion fluid flow rate $Q_{pbp}$ and the control unit is configured to operate the means for regulating flow of the pre-blood pump infusion fluid through the pre-blood pump infusion fluid line such that an emptying time of the fourth container of fresh fluid and the filling time of the waste container are multiples of the same reference time ($T_r$).

2. The apparatus of claim 1, wherein the control unit is configured to calculate N−1 of the set values ($Q_{iset}$) of the fluid flow rates of the at least two fluid lines such that an emptying time of at least one container of fresh fluid connected to the at least two fluid lines is substantially the same as, or a multiple of the emptying time of one or more other containers of fresh fluid connected to the at least two fluid lines, the reference time ($T_r$) being the shortest among the emptying times.

3. The apparatus of claim 1 wherein the control unit is configured to calculate the set values ($Q_{iset}$) of the fluid flow rates of the at least two fluid lines such that at least one of the following conditions is met:

at least two of the emptying time of each container of fresh fluid connected at the other end of the at least two lines selected in the group of fluid lines and the filling time of the waste container are multiples of a same reference time ($T_r$), the emptying time of each container of fresh fluid connected at the other end of the at least two lines selected in the group of fluid lines and the filling time of the waste container are multiples of a first reference time ($T_{r1}$) such that at least two of the emptying time of each container of fresh fluid connected at the other end of the at least two lines selected in the group of fluid lines and the filling time of the waste container that are not multiples of the first reference time ($T_{r1}$) are multiples of a second reference time ($T_{r2}$), at least two of the emptying time of each container of fresh fluid connected at the other end of the at least two lines selected in the group of fluid lines are multiples of a same reference time ($T_r$), and at least two of the emptying time of each container of fresh fluid connected at the other end of the at least two lines selected in the group of fluid lines are multiples of a first reference time ($T_{r1}$) such that at least two of the emptying time of each container of fresh fluid connected at the other end of the at least two lines selected in the group of fluid lines that are not multiples of the first reference time ($T_{r1}$) are multiples of a second reference time ($T_{r2}$).

4. The apparatus of claim 1 wherein the control unit is configured to operate the means for regulating flow through one or more of the at least two fluid lines based on the calculated set values, either automatically or after receipt of a confirmation signal.

5. The apparatus of claim 1 wherein the at least two fluid lines comprise the pre-dilution infusion fluid line, the post-dilution infusion fluid line, and the dialysis liquid infusion line, and wherein the control unit is configured to calculate the set value for fluid flow rate through each of the pre-dilution and the post-dilution infusion fluid lines and the dialysis liquid fluid line such that the emptying time of each of the first container of fresh fluid, the second container of fresh fluid, and the third container of fresh fluid is a multiple of the same reference time ($T_r$).

6. The apparatus of claim 1 wherein the at least two fluid lines comprise the pre-dilution infusion fluid line and the pre-blood pump infusion fluid line, and wherein the control unit is configured to:

operate the blood pump to move blood through the blood withdrawal line;

operate the means for regulating flow of the pre-dilution infusion fluid through the pre-dilution infusion fluid line connected to the blood withdrawal line between a blood pump segment of the blood withdrawal line on which the blood pump acts and the filtration unit;

operate the means for regulating flow of the pre-blood pump infusion fluid through the pre-blood pump infusion fluid line connected to the blood withdrawal line in a region of the blood withdrawal line located between the blood pump segment and an end of the blood withdrawal line opposite an end of the blood withdrawal line connected to the filtration unit; and calculate the set value for the fluid flow rate through each of the pre-dilution infusion fluid line and the pre-blood pump infusion fluid line such that the emptying time of the first container of fresh fluid and the second container of fresh fluid is a multiple of the same reference time $(T_r)$.

7. The apparatus of claim 1 wherein the control unit is configured to operate the means for regulating flow of the effluent fluid through the effluent line connected to the waste container and calculate the set value for the fluid flow rate through each of the fluid lines such that the emptying time of each of the containers of fresh fluid and the filling time of the waste container is a multiple of the same reference time $(T_r)$ and the emptying time of each of the containers of fresh fluid is the same as or a multiple of the emptying time of one or more other containers of fresh fluid.

8. The apparatus of claim 1 wherein, for each of the at least two fluid lines, the control unit is configured to store, in memory connected to the control unit, at least one of a total volume and a total weight of fluid contained in the waste container and each container of fresh fluid to which each of the at least two fluid lines is connected, the control unit further configured to obtain the total volume or total weight of fluid of the waste container and each container of fresh fluid to which each of the at least two fluid lines is connected by one of:

receiving the total weight or the total volume from a sensor associated with each of the waste container and each container of fresh fluid to which each of the at least two fluid lines is connected, wherein each sensor associated with each of the waste container and each container of fresh fluid to which each of the at least two fluid lines is connected is connected to the control unit, receiving the total weight or the total volume for each of the waste container and each container of fresh fluid to which each of the at least two fluid lines is connected from a user interface connected to the control unit, receiving the total volume based on an identification code on each container of fresh fluid to which each of the at least two fluid lines is connected, or retrieving the total weight or the total volume of each container of fresh fluid to which each of the at least two fluid lines is connected from a pre-stored value in memory connected to the control unit;

and wherein the control unit is configured to receive a set value for at least one of:

a treatment time (T) and weight loss (WL) to be achieved during the treatment time;

a treatment dose $(D_{set})$ to be delivered to the patient during the treatment, which comprises a prescribed value for one selected in the group including:

an effluent dose flow rate $(D_{eff\_set})$, which is the prescribed mean value of a flow rate through the effluent line, a convective dose flow rate $(D_{conv\_set})$, which is the prescribed mean value of a sum of flow rates through any infusion fluid line $(Q_{rep}, Q_{pbp})$ and the patient fluid removal rate $(Q_{pfr})$, a diffusive dose flow rate $(D_{dial\_set})$, which is the prescribed mean value of a flow rate through the dialysis liquid fluid line $(Q_{dial})$, a urea dose $(D_{urea\_set})$, which is a prescribed mean value for an estimated urea clearance, and a clearance dose $(K_{solute\_set})$, which is a prescribed mean value for an estimated clearance for a given solute;

the pre-dilution infusion fluid flow rate $(Q_{rep1})$ through the pre-dilution infusion fluid line;

the post-dilution infusion fluid flow rate $(Q_{rep2})$ through the post-dilution infusion fluid line;

the pre-blood pump infusion fluid flow rate $(Q_{pbp})$ through the pre-blood pump infusion fluid line;

the dialysis liquid fluid flow rate $(Q_{dial})$ through the dialysis liquid fluid line;

the effluent fluid flow rate $(Q_{eff})$ through the effluent fluid line; and the patient fluid removal rate $(Q_{pfr})$ from the patient.

9. The apparatus of claim 1 wherein the control unit is configured to:

receive an initial weight or initial volume $(W_i, V_i)$ of the one or more of the containers;

calculate the set value of the fluid flow rate $(Q_{iset})$ in one or more fluid lines of the at least two fluid lines by dividing a weight or volume $(W_i, V_i)$ of the container connected to the one or more fluid lines by the value of the reference time $(T_r)$ using one of the following formulas:

$$Q_{iset}=W_i/T_r \text{ or } Q_{iset}=V_i/T_r.$$

10. The apparatus of claim 9 wherein the control unit is configured to:

receive an initial weight or volume $(W_i, V_i)$ of one or more of the containers;

receive proposed values $(Q_i)$ of the flow rates for the at least two fluid lines;

calculate the set value of the fluid flow rate $(Q_{iset})$ in one or more fluid lines of the at least two fluid lines by dividing a weight or volume $(W_i, V_i)$ of the container connected to the one or more fluid lines by the value of the reference time $(T_r)$ multiplied by a weighing coefficient $(c_i)$ for each container connected to the one or more fluid lines using one of the following formulas: $Q_{iset}=W_i/(T_r \cdot c_i)$, or $Q_{iset}=V_i/(T_r \cdot c_i)$, where the weighing coefficient $(c_i)$ for each container is calculated as a function of an intermediary factor $(b_i)$ obtained by dividing either a dose or a sum of the proposed values $(Q_i)$ of the flow rates by the respective proposed value $(Q_i)$.

11. The apparatus of claim 1 wherein the control unit is configured to:

receive an initial weight or an initial volume $(W_i, V_i)$ of one or more of the containers, receive proposed values $(Q_i)$ of flow rates for the at least two fluid lines;

receive a value of an adjustment parameter (A) defined as a maximum relative change allowed on container change periods;

calculate the set values of fluid flow rates $(Q_{iset})$ based on the proposed values $(Q_i)$, the initial weight or the initial volume $(W_i, V_i)$ of each container and the value of the adjustment parameter (A).

12. The apparatus of claim 1 wherein the control unit is configured to:

receive an initial weight or volume $(W_i, V_i)$ of one or more of the containers;

receive proposed values ($Q_i$) of the flow rates for the at least two fluid lines;

generate, for each pair of lines and respective containers, ratios of interest $R0_k$, which are reference ratios between change periods of pairs of containers and are defined for each pair of lines and respective containers, K being an integer from 1 to M, with the value of M pre-stored in memory connected to a control unit of the apparatus or receivable from a user input;

calculate container change periods $T_i=V_i/Q_i$ or $T_i=W_i/Q_i$ and ranking each circuit according to the calculated container change period, where i=1 to N with $T_i$ increasing with i;

compute all period ratios $R_{ij}=T_i/T_j$, with i>j;

compare each period ratio $R_{ij}$ to the ratios of interest $R0_k$;

verify, for each ratio $R_{ij}$ where a k value exists, a tolerance relation:

$$(1-A)\cdot R_k < R_{ij} < (1+A)\cdot R0_k,$$

compute a number of daily saved container changes;

select the ratios $R_{ij}$ providing a largest number of saved container changes; and apply the ratios of interest corresponding to the selected ratios to calculate the set values ($Q_{iset}$) of the fluid flow rates through the at least two fluid lines.

13. The apparatus of claim 1 wherein the control unit is configured to:

receive a selected treatment time (T); and calculate the reference time ($T_r$) either as the treatment time (T) or as a sub-multiple of the treatment time (T).

14. The apparatus of claim 1 wherein the control unit is configured to:

identify one container of the first, second, third, and fourth containers associated with one fluid line of the at least two fluid lines for which the fluid flow rate has been set; and calculate the reference time ($T_r$) by dividing the initial weight or volume ($W_i$, $V_i$) of the identified container by the set value of the fluid flow rate.

15. The apparatus of claim 1 wherein the control unit is configured to compute the reference time ($T_r$) using one of the following:

dividing a sum of initial weights or volumes ($W_i$, $V_i$) of a plurality of the containers by a prescribed dose flow rate value which is set to be delivered in total through the lines ($D_{conv\_set}$) leading to the same plurality of containers;

dividing the sum of the initial weights or volumes ($W_i$, $V_i$) of all the containers by a total prescribed dose flow rate ($D_{eff\_set}$);

dividing the sum of the initial weights or volumes ($W_i$) of a plurality of the containers by the prescribed dose flow rate value which is set to be delivered in total through the lines ($D_{conv\_set}$) leading to the same plurality of containers, using formula: $T_r=\Sigma W_i\cdot c_i/Dose$, where $c_i$ is a weighing coefficient to be multiplied by the initial weight or volume of each container; and dividing the sum of the initial weights or volumes ($W_i$, $V_i$) of all the containers by the total prescribed dose flow rate ($D_{eff\_set}$), using formula: $T_r=\Sigma W_i\cdot c_i/Dose$, where $c_i$ is the weighing coefficient to be multiplied by the initial weight or volume of each container.

16. The apparatus of claim 1 wherein the control unit is configured to:

associate a reference volume or a reference weight to each container;

compare a measured volume or measured weight of each container to the respective reference volume or reference weight to trigger a container change signal container when the container reaches the respective reference volume or a reference weight;

set, for one or more of the containers of fresh fluid, a reference volume or reference weight which is different from zero or on the waste container a reference volume or weight which is less than the maximum volume or maximum weight of the waste container.

17. The apparatus of claim 16 wherein the control unit is configured to calculate a set value ($V_{eff\text{-}change}$) of the waste container reference volume or reference weight at which the waste container is full such that a filling time of the waste container is one of: substantially the same as, proportional to, or a multiple of the emptying time of one or more of the containers of fresh fluid.

18. The apparatus of claim 4 wherein, when the at least two fluid lines comprise the pre-dilution infusion fluid line, the means for regulating the flow of pre-dilution infusion fluid comprises a pre-dilution infusion fluid pump;

wherein, when the at least two fluid lines comprise the post-dilution infusion fluid line, the means for regulating the flow of post-dilution infusion fluid comprises a post-dilution infusion fluid pump;

wherein, when the at least two fluid lines comprise the dialysis liquid fluid line, the means for regulating the flow of dialysis liquid comprises a dialysis fluid pump; and wherein, when the at least two fluid lines comprise the pre-blood pump infusion fluid line, the means for regulating the flow of pre-blood pump infusion fluid comprises a pre-blood infusion fluid pump.

19. The apparatus of claim 1 wherein the control unit is configured to receive at least one of:

a fluid removal rate ($Q_{pfr}$) from the patient, a treatment time (T), and a weight loss (WL) to be imposed over the treatment time (T) and calculate a patient fluid removal rate ($Q_{pfr}$) as a ratio of weight loss divided by treatment time (WL/T);

and wherein the control unit is configured to calculate the set values ($Q_{iset}$) of the fluid flow rates through the at least two fluid lines such that:

emptying times of the containers of fresh fluid are multiples of a same reference time ($T_r$), and a sum of the fluid flow rates ($Q_{rep1}$, $Q_{rep2}$, $Q_{pbp}$) through the infusion fluid lines connected to the first, second, and fourth containers plus the fluid flow rate ($Q_{dial}$) through the dialysis liquid fluid line, if connected, plus the fluid removal rate ($Q_{pfr}$) from the patient equals the effluent fluid flow rate ($Q_{eff}$) through the effluent fluid line.

20. The apparatus of claim 1 wherein the at least two fluid lines comprise the post-dilution infusion fluid line and the pre-blood pump infusion fluid line, wherein the fourth container contains an anticoagulant comprising a citrate solution, and the second container leading to the post-dilution infusion fluid line comprises an ionic balance solution comprising a calcium ion based solution, and wherein the control unit is configured to calculate and regulate fluid flow rate through the pre-blood pump infusion fluid line and through the post-dilution infusion fluid line based on a pre-defined algorithm.

21. The apparatus of claim 1 wherein every container of fresh fluid to which each of the at least two fluid lines is connected contain a fluid having a same composition.

22. The apparatus of claim 1 wherein the control unit is configured to receive a minimum volume of fluid which may be contained in each container of fresh fluid and a maximum volume of fluid which may be contained in the waste container, and wherein the control unit is further configured to active an alarm to generate an alarm signal or stop the treatment when one of the following events happens:
the minimum volume of fluid in one of the fresh fluid containers is detected, or
the maximum volume of fluid in the waste container is detected.

23. The apparatus of claim 1 wherein the control unit is configured to:
calculate the set values ($Q_{iset}$) of the fluid flow rates through N−1 of the at least two fluid lines such that an emptying time of at least one among the first, second, third, and fourth containers of fresh fluid is substantially the same as, or a multiple of one time selected among: an emptying time of one or more of the other containers of fresh fluid, and a filling time of the waste container, the reference time being the shortest among the emptying times and the filling time, and
calculate the remaining of the set values ($Q_{iset}$) of the fluid flow rates through the at least two fluid lines such that the sum of the fluid flow rates through fluid lines coming from the first, second, third, and fourth fresh fluid containers and of a patient fluid removal rate ($Q_{pfr}$) is equal to the effluent fluid line flow rate ($Q_{eff}$).

24. The apparatus of claim 1 wherein the control unit is configured to:
calculate the set values ($Q_{iset}$) of the fluid flow rates through N−1 of the at least two fluid lines such that an emptying time of at least one among the first, second, third, and fourth containers of fresh fluid is substantially the same as, or a multiple of a filling time of the waste container, and
calculate the remaining of the set values ($Q_{iset}$) of the fluid flow rates through the at least two fluid lines such that the sum of the fluid flow rates through fluid lines coming from the first, second, third, and fourth fresh fluid containers and of a patient fluid removal rate ($Q_{pfr}$) is equal to the effluent fluid line flow rate ($Q_{eff}$).

25. The apparatus of claim 1 wherein the control unit is configured to
receive an initial weight or an initial volume ($W_i$, $V_i$) of one or more of the containers from a scale configured to weigh the one or more containers; and
calculate the set value ($Q_{iset}$) of the fluid flow rate in one or more fluid lines of the at least two fluid lines by dividing the initial weight or the initial volume ($W_i$, $V_i$) of the respective container by the value of the reference time ($T_r$) multiplied by a respective weighing coefficient ($c_i$) for each respective container using one of the following formulas: $Q_{iset}=W_i(T_r \cdot c_i)$ or $Q_{iset}=W_i/(T_r \cdot c_i)$.

26. An apparatus for extracorporeal treatment of fluid comprising:
a filtration unit having a primary chamber and a secondary chamber separated by a semi-permeable membrane;
a blood withdrawal line connected to an inlet of the primary chamber, and a blood return line connected to an outlet of the primary chamber, the blood withdrawal line and the blood return line configured to connect to a patient cardiovascular system;
a blood pump configured to control the flow of blood through the blood withdrawal line and the blood return line;
an effluent fluid line connected, at one end thereof, to an outlet of the secondary chamber and at its other end to a waste container, wherein effluent fluid flowing through the effluent fluid line comprises an effluent fluid flow rate ($Q_{eff}$);
at least two fluid lines selected from the group of fluid lines comprising:
a pre-dilution infusion fluid line connected at one end thereof to the blood withdrawal line and at its other end to a first container of fresh fluid,
a post-dilution infusion fluid line connected at one end thereof to the blood return line and at its other end to a second container of fresh fluid,
a dialysis liquid fluid line connected at one end thereof to an inlet of the secondary chamber and at its other end to a third container of fresh fluid,
a pre-blood pump infusion fluid line connected at one end thereof to a fourth container of fresh fluid and at its other end to the blood withdrawal line in a region of the pre-blood pump infusion fluid line which is positioned in use upstream the blood pump;
a control unit configured to:
receive an initial weight or volume ($W_i$, $V_i$) of one or more of the first, second, third, and fourth containers of fresh fluid;
receive proposed values ($Q_i$) of the flow rates for the fluid lines;
generate, for each pair of fluid lines and containers of fresh fluid connected to the fluid lines, ratios of interest $R0_k$, which are reference ratios between change periods of pairs of containers and are defined for each pair of fluid lines and containers of fresh fluid connected to the fluid lines, K being an integer from 1 to M, with the value of M pre-stored in memory connected to the control unit or received by the control unit from a user input;
calculate container change periods $T_i=V_i/Q_i$ or $T_i=W_i/Q_i$ and ranking each circuit according to the calculated container change period, where i=1 to N with $T_i$ increasing with i;
compute all period ratios $R_{ij}=T_i/T_j$, with i>j;
compare each period ratio $R_{ij}$ to the ratios of interest $R0_k$;
verify, for each ratio $R_{ij}$ where a k value exists, a tolerance relation: $(1-A) \cdot R0_k < R_{ij} < (1+A) \cdot R0_k$, and compute a number of daily saved container changes;
select the ratios $R_{ij}$ providing a largest number of saved container changes;
apply the ratios of interest corresponding to the selected ratios to compute a set value ($Q_{iset}$) of the fluid flow rate for each fluid line of the at least two fluid lines; and
regulate fluid flow through each fluid line of the at least two fluid lines based at least in part on the set values ($Q_{iset}$) of each fluid line of the at least two fluid lines;
wherein, when the at least two fluid lines comprise the pre-dilution infusion fluid line, one set value ($Q_{iset}$) of the computed set values ($Q_{iset}$) comprises the pre-dilution infusion fluid flow rate $Q_{rep1}$ and the control unit is configured to regulate flow of the pre-dilution infusion fluid through the pre-dilution infusion fluid line to a pre-dilution infusion fluid flow rate ($Q_{rep1}$) using means connected to the control unit for regulating flow of the pre-dilution infusion fluid through the pre-dilution infusion fluid line;

wherein, when the at least two fluid lines comprise the post-dilution infusion fluid line, one set value ($Q_{iset}$) of the computed set values ($Q_{iset}$) comprises the post-dilution infusion fluid flow rate ($Q_{rep2}$) and the control unit is configured to regulate flow of the post-dilution infusion fluid through the post-dilution infusion fluid line to a post-dilution infusion fluid flow rate ($Q_{rep2}$) (using means connected to the control unit for regulating flow of the post-dilution infusion fluid through the post-dilution infusion fluid line;

wherein, when the at least two fluid lines comprise the dialysis liquid fluid line, one set value ($Q_{iset}$) of the computed set values ($Q_{iset}$) comprises the dialysis liquid fluid flow rate ($Q_{dial}$) and the control unit is configured to regulate flow of the dialysis liquid through the dialysis liquid fluid line to a dialysis liquid fluid flow rate ($Q_{dial}$) using means connected to the control unit for regulating flow of the dialysis liquid through the dialysis liquid fluid line; and wherein, when the at least two fluid lines comprise the pre-blood pump infusion fluid line, one set value ($Q_{iset}$) of the computed set values ($Q_{iset}$) comprises the pre-blood pump infusion fluid flow rate ($Q_{pbp}$) and the control unit is configured to regulate flow of the pre-blood pump infusion fluid through the pre-blood pump infusion fluid line to a pre-blood pump infusion fluid flow rate ($Q_{pbp}$) using means connected to the control unit for regulating flow of the pre-blood pump infusion fluid through the pre-blood pump infusion fluid line.

27. The apparatus of claim 26 wherein the control unit is configured to regulate fluid flow through each fluid line of the at least two fluid lines based at least in part on the set values ($Q_{iset}$) either automatically or after receipt of a confirmation signal.

28. The apparatus of claim 26 wherein the at least two fluid lines comprise the pre-dilution infusion fluid line, the pre-blood pump infusion fluid line, and the dialysis liquid fluid line, and wherein the control unit is configured to calculate the set value for fluid flow rate through each of the pre-dilution and the post-dilution infusion fluid lines and the dialysis liquid fluid line such that the emptying time of each of the first container of fresh fluid, the second container of fresh fluid, and the third container of fresh fluid is a multiple of the same reference time ($T_r$).

* * * * *